United States Patent [19]

Greatbatch et al.

[11] Patent Number: 5,324,643
[45] Date of Patent: Jun. 28, 1994

[54] METHOD OF CONFERRING RESISTANCE TO RETROVIRAL INFECTION

[75] Inventors: Wilson Greatbatch, Akron; John C. Sanford, Geneva, both of N.Y.

[73] Assignee: Greatbatch Gen-Aid, Ltd., Clarence, N.Y.

[21] Appl. No.: 739,718

[22] Filed: Jul. 29, 1991

Related U.S. Application Data

[63] Continuation-in-part of Ser. No. 156,188, Feb. 16, 1988, abandoned.

[51] Int. Cl.$^5$ .............. C12N 15/11; C12N 5/10; C07H 21/02; C07H 21/04
[52] U.S. Cl. ................ 435/91.32; 435/91.1; 435/91.3; 435/172.3; 435/240.1; 435/240.2; 536/23.1; 935/3; 935/6; 935/34; 935/70
[58] Field of Search ............. 435/172.3, 240.1, 240.2, 435/91, 91.1, 91.3, 91.32; 536/27, 23.1

[56] References Cited

U.S. PATENT DOCUMENTS 4,806,463  2/1989  Goodchild et al. ............... 435/5

FOREIGN PATENT DOCUMENTS

WO8703451  6/1987  PCT Int'l Appl. .

OTHER PUBLICATIONS

H. Mitsuya et al. (1987), Nature 325: 773-778.
E. C. M. Mariman (1985) Nature 318: 414.
R. Tellier et al. (1985) Nature 318: 414.
L.-J. Chang et al (1987) J. Virology 61(3): 921-924.
I. Herskowitz (1987) Nature 329: 219-222.

Primary Examiner—Jacqueline Stone
Assistant Examiner—Johnny F. Railey, II
Attorney, Agent, or Firm—Hodgson, Russ, Andrews, Woods & Goodyear

[57] ABSTRACT

In accordance with the present invention, disclosed is a method of conferring, upon a host cell, resistance to retroviral infection by interfering with one or more of the infection processes including retroviral replication and assembly into infective viral particles. The method involves introducing a vector into a host cell, wherein the vector comprises a polynucleotide which directs transcription, within the host cell, of RNA which is a) complementary or homologous, depending on the target region, to a nucleic acid sequence within one or more regions of the genome of the retrovirus; and b) is effective in inhibiting retroviral replication and/or interfering with assembly into viral particles when the host cell is infected. Also disclosed is a method of treatment using cells upon which resistance to infection has been conferred.

34 Claims, 19 Drawing Sheets

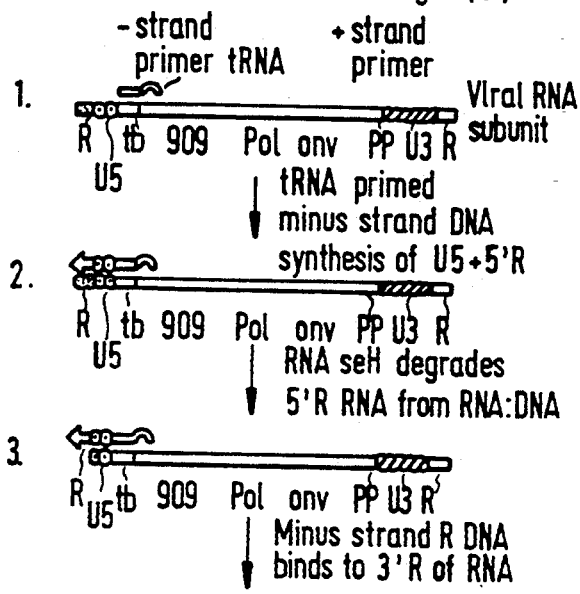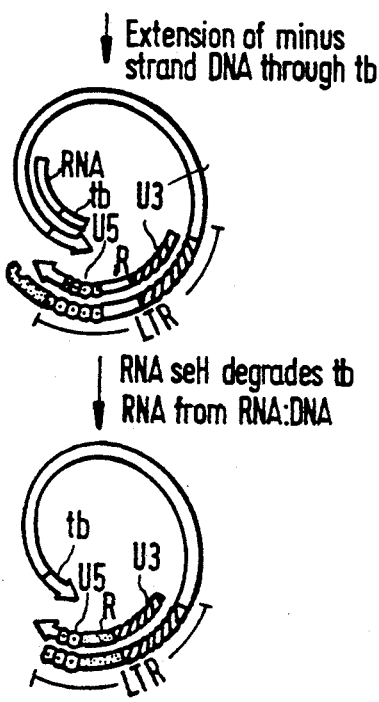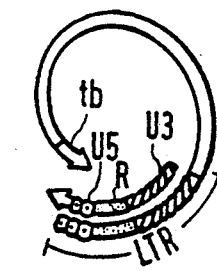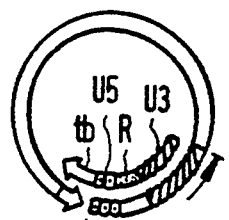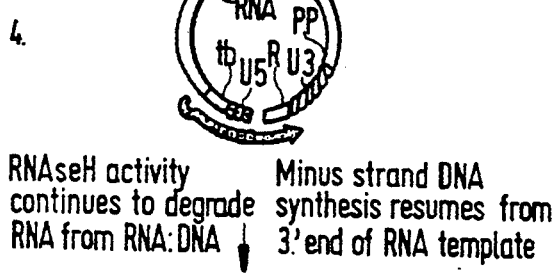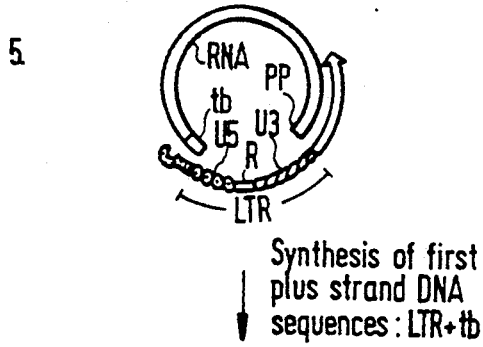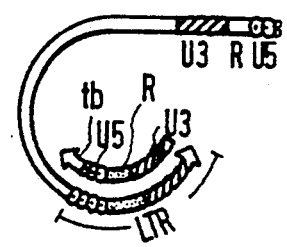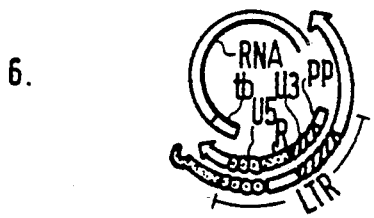
FIG. 1A DNA Synthesis BAM H1, HIND III-RESTRICTION ENDONUCLEASES ANTI-PBS, ANTI-R, ANTI-S, ANTI-AUG,
ANTI-SENSE CONSTRUCTS
BOX A, BOX B - Pol III PROMOTER   T's - PROMOTER TERMINATION

FIG. 2 HIV LTR Genome

GGUCUCUCUGGUUAGACCAGAUCUGAGCCUGGGAGCUCUCUGGCUAACUAGGGAACCCACUGCUUA

AGCCUCAAUAAAGCUUGCCUUGAGUGCUUCAAGUAGUGUGUGCCCGUCUGUUGUGUGACUCUGGUA

ACUAGAGAUCCCUCAGACCCUUUUAGUCAGUGUGGAAAAUCUCUAGCAGUGGCGCCCGAACAGGGA

CCUGAAAGCGAAAGGGAAACCAGAGCUCUCUCGACGCAGGACUCGGCUUGCUGAAGCGCGCACGGC

AAGAGGCGAGGGGCGGCGACUGGUGAGUACGCCAAAAAUUUUGACUAGCGGAGGCUAGAAGGAGAG
  270

MetGlyAlaArgAlaSerValLeuSerGlyGlyGluLeuAspArgTrpGluLysIleArgLeu
AGAUGGGUGCGAGAGCGUCAGUAUUAAGCGGGGGAGAAUUAGAUCGAUGGGAAAAAAUUCGGUUA

ArgProGlyGlyLysLysLysTyrLysLeuLysHisIleValTrpAlaSerArgGluLeuGluArg
AGGCCAGGGGGAAAGAAAAAAUAUAAAUUAAAACAUAUAGUAUGGGCAAGCAGGGAGCUAGAACGA

PheAlaValAsnProGlyLeuLeuGluThrSerGluGlyCysArgGlnIleLeuGlyGlnLeuGln
UCCGCAGUUAAUCCUGGCCUGUUAGAAACAUCAGAAGGCUGUAGACAAAUACUGGGACAGCUACAA

ProSerLeuGlnThrGlySerGluGluLeuArgSerLeuTyrAsnThrValAlaThrLeuTyrCys
CCAUCCCUUCAGACAGGAUCAGAAGAACUUAGAUCAUUAUAUAAUACAGUAGCAACCCUCUAUUGU

ValHisGlnArgIleGluIleLysAspThrLysGluAlaLeuAspLysIleGluGluGluGlnAsn
GUGCAUCAAAGGAUAGAGAUAAAAGACACCAAGGAAGCUUUAGACAAGAUAGAGGAAGAGCAAAAC

LysSerLysLysLysAlaGlnGlnAlaAlaAlaAspThrGlyHisSerSerGlnValSerGln
AAAAGUAAGAAAAAAGCACAGCAAGCAGCAGCUGACACAGGACACAGCAGUCAGGUCAGCC

FIG. 3  HTLV-1 LTR Genome

```
GGCUCGCAUCUCUCCUCCACGCGCCCGCCACCCUACCUGAGGCCUCCAUCCACGCCGAUUGAGUCG
         10        20        30        40        50        60

CGUUCUGCCGCCUCCCGCCUGUGGUGCCUCCUGAACUGCGUCCGCCGUCUAGGUAAGUUUAAAGCU
    70        80        90       100       110       120       130

CAGGUCGAGACCGGGCCUUUGUCCGGCGCUCCCUUGGAGCCUACCUAGACUCAGCCGGCUCUCCAC
         140       150       160       170       180       190

GCUUUGCCUGACCCUGCUUGCUCAACUCUACGUCUUUGUUUCGUUUUGUGUUCUGCGCCGUUACAG
    200       210       220       230       240       250       260

AUCGAAAGUUCCACCCCUUUCCCUUUCAUUCACGACUGACUGCCGGCUUGGCCCACGGCCAAGUAC
    270

CGGCGACUCCGUUGGCUCGGAGCCAGCGACAGCCCAUCCUAUAGCACUCUCAGGAGAGAAAUUUAG
                                   360
             B                                          GlyGlnIle
UACACAGUUGGGGGCUCGUCCGGGAUACGAGCGCCCCUUUAUUCCCUAGGCAAUGGGCCAAAUCUU

PheSerArgSerAlaSerProIleProArgProProArgGlyLeuAlaAlaHisHisTrpLeuAsn
   UUCCCGUAGCGCUAGCCCUAUUCCGCGACCGCCCCGGGGGCUGGCCGCUCAUCACUGGCUUAAC

PheLeuGlnAlaAlaTyrArgLeuGluProGlyProSerSerTyrAspPheHisGlnLeuLysLys
   UUCCUCCAGGCGGCAUAUCGCCUAGAACCCGGUCCCUCCAGUUACGAUUUCCACCAGUUAAAAAA

PheLeuLysIleAlaLeuGluThrProAlaArgIleCysProIleAsnTyrSerLeuLeuAlaSer
   UUUCUUAAAAUAGCUUUAGAAACACCGGCUCGGAUCUGUCCCAUUAACUACUCCCUCCUAGCCAGC
                                   630
LeuLeuProLysGlyTyrProGlyArgValAsnGluIleLeuHisIleLeuIleGlnThrGln
   CUACUCCCAAAAGGAUACCCCGGCCGGGUGAAUGAAAUUUUACACAUACUCAUCCAAACCCA
                                                              720
```

FeLV LTR Genome                    FIG. 4

MLV  CCCTGTGCCTT           ATTTCAACTAACCAATC   A  G   T  TCGCTTCTCGCTTCT
FeLV AATTCAACCTTCCGTCTCATTTAAACTAACCAATCCCCACGCGTCTCGCTTCT

GTTCGCGCGCTTCCGTCCCCGAGCTCAATAAAA    GAGCCCACAACCCCTCACTCGGCG
                                                    -5
     GTACGCGCGCTT   TCT    GCT   ATAAAAAACGAGCCATCAGCCCC  CACA GGCG

CGCCAGTCCTCCGATTGACTGAGTCCCCCGCGTACCCGTGTATCCAATAAACCCTCTTGC
                                                50
     CGCAAGTCTTTGTTGAGACTTCACCCCCCGCGTACCCGTGTA CGAATAAAGCCTCTTGC

AGTT GCATCCGACTTGTGGTCTCGGTGTTCCTTGGG A  GGGTCTCCTCT  GAGTGA
                                         100
     TGTTTGCATCTGACTCGTGGTCTCGGTGCTCCGTGGGCACGGGGTCTCATCGCGGAG GA

TTGAC TACCCGTCAGCGGGGGTCTTTCATTTGGGGCTCGTCCGGGATCGGGAGACCCC
                                         150
     A GACCTAC   TC  CGGGGGTCTTTCATTTGGGGGCTCGTCCGGGAT A GAGACCCC

TG   CCCAGGGACCACCGACCCACCACCGGGAGGTAAGCTGGCCAGCAAC TTATCTGTG
                                         200
     CAACCCCAGGGACCACCGACCCACCATCAGGAGGTAAGCTGGCCGGCGACCATATCTGT

TCTGTCCGATTGTCT AGTGTCTATG  ACT     GATTTTATGCGCCTGCGTCGGTA
                                  250
         TGTCC   TTGTGTAAGTGTCTCTGTCAACTGATCTGATTTT

LeuThrSerSerValSerGlyGly ProValValGluLeuThrSerSerGlu
       CTAGTTAGCTAACTAGCTCTGTATCTGGCGGA CCCGTGGTGGAACTGACGAGTTCGGAA

GGCGGTGGAACCGAAGGAGCTGACGAGCTCGTAC

HisProAlaAlaThrLeuGlyAspValPro Gly  Thr    SerGlyAlaValPhe
     CACCCGGCCGCAACCCTGGGAGACGTCCCA GGG  ACT    TCGGGGCCGTTTTT

TCCGCCCCCGCAACCCTGGAAGACGTTCCACGGGTGTCTGATGTCTGGAGCC TCT A
                                                        MetSerGlyAla Ser

ValAlaArgProGluSerLysAsnProAspArgPheGlyLeuPheG..
     GTGGCCCGACCTGAGTCCAAAAATCCCGATCGTTTTGGACTCTTTG..

AGTGGG  ACA   G CC ATT GGG GCTCAT    CTGTTTG..
     SerGly  Thr   Ala  Ile Gly AlaHis    LeuPheG..

TABLE 1

FIG. 5

| | Anti-HIV Sequence name | Anti-HIV Sequence | HIV target site | Modes of Action |
|---|---|---|---|---|
| 1. | Anti-R | 1-97 (minus strand) | 3'R-region of viral RNA and of mRNA | Block "1st jump" of reverse transcription TAT binding and translation of mRNA |
| 2. | R homolog | 1-97 (plus strand) | 3'R-region of minus strand cDNA | Block "1st jump" of reverse transcription |
| 3. | Anti-PBS | 170-210 (minus strand) | PBS site of viral RNA and of plus strand cDNA | Block initiation of reverse transcription and "2nd jump" |
| 4. | PBS homolog | 182-199 (plus strand) | 3'PBS region of minus strand cDNA | Block "2nd jump" of reverse transcription |
| 5. | False primer | Lys tRNA (with 3' 18 bp substitution) | Any new PBS site of viral RNA | Initiate reverse transcription at improper site |
| 6. | False template | PBS homolog (with 5' false tail) | Primer complex and secondary site | "Disarm" primers, produce antiviral cDNA |
| 7. | Polypurine homolog | 8630-8670 (plus strand) | Polypurine complement in minus strand cDNA | Block proper initiation of plus strand DNA synthesis |
| 8. | Anti-S | 270-340 (minus strand) | Acceptor site for 1st TAT splice and GAG initiation codon of mRNA | Block splicing needed for TAT translation and initiation of GAG translation |
| 9. | Anti-TAT-S | 5340-5430 (minus strand) | Donor site for 1st TAT splice and TAT initiation codon of mRNA | Block splicing needed for TAT translation and initiation of TAT translation |
| 10. | Anti-TAT-S | 5610-5640 (minus strand) | Acceptor site for 2nd TAT splice of mRNA | Block mRNA splicing needed for TAT translation |
| 11. | Anti-TAT-S | 7940-7970 (minus strand) | Donor site for 2nd TAT splice of mRNA | Block of mRNA splicing needed for TAT translation |
| 12. | TAT repressor | 5530-5593 (plus strand) | 5'end of mRNA | Block binding of TAT activator |
| 13. | ART repressor | 7956-8080 (plus strand) | ART binding site of mRNA | Block binding of ART activator |

FIG. 6  HTLV-1  Anti-R Gene Construct

```
GAAAC  AAAGA  CGTAG  AGTTG  AGCAA  ACAGG            COM
CTTTG  TTTCT  GCATC  TCAAC  TCGTT  CGTCC            REV
```

Anti-CAP Gene Construct

```
GTGAA  GGAGA  GATGC  GAGCC                          COM
CACTT  CCTCT  CTACG  CTCGG                          REV
```

FIG. 7  FeLV  Anti-R Gene Construct

```
GATGC  AAACA  GCAAG  AGGCT  TTATT  CGTAC  ACGGG     COM
CTACG  TTTGT  CGTTC  TCCGA  AATAA  GCATG  TGCCC     REV

TACCC  GGGCG  GTCAA  GTCTC  AACAA  AGACT  TGCGC     COM
ATGGG  CCCGC  CAGTT  CAGAG  TTGTT  TCTGA  ACGCG     REV
```

FIG. 8  HIV  Anti-R Gene Construct

```
ACTTG  AAGCA  CTCAA  GGCAA  GCTTT  ATTGA  GGCTT     COM
TGAAC  TTCGT  GAGTT  CCGTT  CGAAA  TAACT  CCGAA     REV

AAGCA  GAGGG  TTCCC  TAGTT  AGCCA  GAGAG  CTCCC     COM
TTCGT  CACCC  AAGGG  ATCAA  TCGGT  CTCTC  GAGGG     REV

AGGCT  CAGAT  CTGGT  CTAAG  CAGAG  AGACC            COM
TCCGA  GTCTA  GACCA  GATTC  GTCTC  TCTGG            REV
```

FIG. 9  FeLV     Anti-PBS Gene Construct

```
GGGTC TCTAT CCCGG ACGAG CCCCC AAATC        COM
CCCAG AGATA GGGCC TGCTC GGGGG TTTAG        REV
```

FIG. 10  HTLV-1    Anti-PBS Gene Construct

```
GCGCT CGTAT CCCGG ACGAG CCCCC AACTG        COM
CGCGA GCATA GGGCC TGTCT GGGGG TTGAC        REV
```

FIG. 11  HIV     Anti-PBS Gene Construct

```
5'  GTCCC TGTTC GGGCG CCACT GCTAG  3'
3'  CAGGG ACAAG CCCGC GGTGA CGATC  5'
```

FIG. 12  FeLV     Anti-AUG Gene Construct

```
5'  CTAGA GGCTC CAGAC ATCAG ACACC CGTGG  3'
3'  GATCT CCGAG GTCTG TAGTC TGTGG GCACC  5'
```

FeLV     Anti-S Gene Construct

```
5'  TCGCC GGCCA GCTTA CCTCC TGATG GTGGG  3'
3'  AGCGG CCGGT CGAAT GGAGG ACTAC CACCC  5'
```

FIG.13    HTLV-1    Anti-S Gene Construct

5'    CTTTA  AACTT  ACCTA  GACGG  CGGAC  GCAGT    3'
3'    GAAAT  TTGAA  TGGAT  CTGCC  GCCTG  CGTCA    5'

Anti-AUG Gene Construct

5'    AGATT  GGCCC  ATTGC  CTAGG  GAATA  AAGGG    3'
3'    TCTAA  CCGGG  TAACG  GATCC  CTTAT  TTCCC    5'

FIG.14    HIV    Anti-S, Anti-GAG & Anti-AUG Gene Construct

5'    TGACG  CTCTC  GCACC  CATCT  CTCTC  CTTCT  AGCCT    3'
3'    ACTGC  GAGAG  CGTGG  GTAGA  GAGAG  GAAGA  TCGGA    5'

5'    CCGCT  AGTCA  AAATT  TTTGG  CGTAC  TCACC  AGTCG    3'
3'    GGCGA  TCAGT  TTTAA  AAACC  GCATG  AGTGG  TCAGC    5'

Recombinant Plasmid pGB-neo-H(1)

Recombinant Plasmid pGB-neo-H(2)

Recombinant Plasmid pGB-neo B(1)

Recombinant Plasmid pGB-neo B(2)

CONSTRUCTION OF RSV VECTOR FAMILY

HIV Gene Construct
Anti-PBS, Anti-AUG, Anti-GAG, Anti-S.D.

```
GATCC  TAGTC  AGACA  GGCTT  TTCAG  GTCCC  TGTTC  GGGGG
----G  ATCAG  TCTGT  CCGAA  AAGTC  CAGGG  ACAAG  CCCGC
-BAMHI .....  BOXA..                    .....Anti-PBS .....

CCACT  GCTAG  GAGAT  CAACT  CCAGT  TGACG  CTCTC  GCACC
GGTGA  CGATC  CTCTA  GTTGA  GGTCA  ACTGC  GAGAG  CGTGG
              .....BOXB..                 ------------------

CATCT  CTCTC  CTTCT  AGCCT  CCGCT  AGTCA  AAATT  TTTGG
GTAGA  GAGAG  GAAGA  TCGGA  GGCGA  TCAGT  TTTAA  AAACC
-------------------------------------------------------

CGTAC  TCACC  AGTCG  CCGCC  CCTCG  TTTTT  TTTTT  A----
GCATG  AGTGG  TCAGC  GGCGG  GGAGC  AAAAA  AAAAA  TTCGA
-----------        -------------  .STOP.  .....  HIND3
```

HIV-Gene Construct
Anti-R, Anti-PBS

```
AGCTT  TGGCA  TAGTT  GGCTT  TTCAG  GTCCC  TGTTC  GGGCG
----A  ACCGT  ATCAA  CCGAA  AAGTC  CAGGG  ACAAG  CCCGC
HIND3  .....  BOXA.....                  ----Anti-PBS -----

CCACT  GCTAG  GAGTT  CGAGA  CCAGT  ACTTG  AAGCA  CTCAA
GGTGA  CGATC  CTCAA  GCTCT  GGTCA  TGAAC  TTCGT  GAGTT
              .....BOXB...                ----Anti-R---------

GGCAA  TCTTT  ATTGA  GGCTT  AAGCA  GTGGG  TCCCC  TAGTT
CCGTT  AGAAA  TAACT  CCGAA  TTCGT  CACCC  AAGGG  ATCAA
-----------------------------------------Anti-R---------

AGCCA  GAGAG  CTCCC  AGGCT  CAGAT  CTGGT  CTAAC  CAGAG
TCGGT  CTCTC  GAGGG  TCCGA  GTCTA  GACCA  GATTG  GTCTC
-----------------------------------------Anti-R---------

AGACC  TTTTT  TTTTT  G----
TCTGG  AAAAA  AAAAA  CCTAG
-----  ...STOP....   BamHI
```

FIG. 22

FeLV Gene Construct
Anti-R & Anti-PBS

```
GATCC  TTGGC  ATAGT  TGGCT  GGGTC  TCTAT  CCCGG  ACGAG
----G  AACCG  TATCA  ACCGA  CCCAG  AGATA  GGGCC  TGGTC
BamHI  ----BOXA----   ----   ........Anti - PBS.......

CCCCC  AAATC  GGAGT  TCGAG  ACCAG  GATGC  AAACA  GCAAG
GGGGG  TTTAG  CCTCA  AGCTC  TGGTC  CTACG  TTTGT  CGTTC
............  --------BOXB---------------------------

AGGCT  TTATT  CGTAC  ACGGG  TACCC  GGGCG  GTCAA  GTCTC
TCCGA  AATAA  GCATG  TGCCC  ATGGG  CCCGC  CAGTT  CAGAG
..... Anti -  R...    ....  ..........................

Bcl1
AACAA  AGACT  TGATC  ATTTT  TTTTT  A----
TTGTT  TCTGA  ACTAG  TAAAA  AAAAA  TTCGA
....   ...........  ---STOP------ .Hind3
```

FeLV Gene Construct
Anti-PBS, Anti-AUG, Anti-S.D.

```
AGCTT  GCAGT  CAGAC  AGGCA  CTATC  CCGGA  CGAGC  OCCCCA
----A  CGTCA  GTCTG  TCCGT  GATAG  GGCCT  GCTCG  GGGGT
Hind3  .....BOX A .......  ----------Anti  PBS------

AATGA  GAGTT  CAACT  CCAGT  TCGCC  GGCCA  GCTTA  CCTCC
TTACT  CTCAA  GTTGA  GGTCA  AGCGG  CCGGT  CGAAT  GGAGG
-----  .....  BOX B......   -----  SPLICE DONOR SITE--

TGATG  GTGGG  CTAGA  OGGCTC  CAGAC  ATCAG  ACACC  CGCGG
ACTAC  CACCC  GATCT  CCGAG   GTCTG  TAGTC  TGTGG  GCGCC
------------  ..............  ...AUG SITE..............

TTTTT  TTTTT  G----
AAAAA  AAAAA  CCTAG
---STOP-----  BamHI
```

FIG. 23

HTLV-1 Gene Construct
Anti-PBS, S.D. & AUG

```
          10          20          30          40
GATCC GAGTC AGACA GGCTT TTCAG GTATC CCCGG ACGAG
----G CTCAG TCTGT CCGAA AAGTC CATAG GGGCC TGCTC
 Bam  -------BOXA---              .........Anti-PBS..

50          60          70          80
CCCCC AACTG GAGGT CGAGA CCAGT CGTAG AACTT ACCTA
GGGGG TTGAC CTCCA GCTCT GGTCA GCATC TTGAA TGGAT
............ ------BOX B-------   .........Anti- S.D..

90         100         110         120
GACGG CGCAC GCAGT AGATT GGCCC ATTGC CCAGG GAATA
CTGCC GCGTG CGTCA TCTAA CCGGG TAACG GGTCC CTTAT
.................         ---------Anti-AUG---------

130         140
AAGGG TTTTT TTTTT A----
TTCCC AAAAA AAAAA TTCGA
-----  ....STOP...  hind3
```

HTLV-1 Gene Construct
Anti-R

```
          10          20          30          40
AGCTT TGGCA TAGTT GGCTT GCGTT CGTAT CCCGG ACGAG
----A ACCGT ATCAA CCGAA CGCGA GCATA GGGCC TGCTC
Hind3  ......BOX A...   ---------------Anti-PBS---

50          60          70          80
CCCCC AACTG GAGTT CGAGA CCAGT GTGAA GGAGA GATGC
GGGGG TTGAC CTCAA GCTCT GGTCA CACTT CCTCT CTACG
-----------   .... BOXB...    --------Anti-CAP---

90         100         110         120
GAGCC CTTTA AACTT ACCTA GACGG CGGAC GCAGT GAAAC
CTCGG GAAAT TTGAA TGGGT CTGCC GCCTG CGTCA CTTTG
-----  .....Anti-S.D......  ..Anti-S.D. (contd.) ----

130         140         150         160
AAAGA CGTAG AGTTA AGCAA GCAGG TTTTT TTTTT C----
TTTCT GCATC TCAAC TCGTT CGTCC AAAAA AAAAA GCTAG
---Anit-R/Anti-AUG --------------  STOP  STOP -Bam
```

FIG. 24

8 SEGMENTS

METHOD OF CONFERRING RESISTANCE TO RETROVIRAL INFECTION

CROSS-REFERENCE TO RELATED APPLICATIONS

This application is a continuation-in-part application of U.S. Ser. No. 156,188, filed Feb. 16, 1988, now abandoned, which is incorporated herein by reference.

FIELD OF THE INVENTION

The present invention related generally to the inhibition of retroviral replication and other essential retroviral functions by hybridization interference in a host cell system. More particularly, the invention provides compositions and methods for producing RNA conplementary or homologous to essential retrovirus replication sites within the retrovirus genome.

BACKGROUND OF THE INVENTION

Retroviruses are the causative agents for an increasing number of diseases of higher organisms including: AIDS, HIV, various leukemias, feline leukemia, murine leukemia, several avian leukemias, various sarcomas of mice, rats, monkeys, birds, and cats, and other lymphotrophic diseases of man, including Adult T-Cell leukemia. Acquire Immune Deficiency Syndrome (AIDS), the recently most noteworthy of these diseases, is caused by a retrovirus which has been called HTLV-III, LAV, RAV or most recently HIV. Coffin et al, Science, 232:697 (1986). HIV is one of a group of retroviral diiseases which attacks the T4 lymphocytes thereby destroying the body's immune system. Anderson, Science, 226:401-409 (1984); Weiss, In RNA Tumor Viruses-II, vol. 2, Cold Spring Harbor Laboratory, pp. 405-485 (1985). The disease is uniformly fatal and no cure has been developed which either kills the virus in situ or replaces the lost elements of the body's immune system. Some experimental drugs such as HPA-23, azidothymidine and suramin show limited effects in stopping the virus, and immunimodulators such as thymostimulin and isoprinosine hopefully will bolster the patient's malfunctioning immune system, but to date there is no proven therapy or cure for the AIDS patient. It is also unlikely that a traditional vaccine for the virus will be developed for quite some time due to the wide variation in antigenicity of various strains of the virus.

Retroviral diseases differ from many other viral diseases in that the infective agent, a retrovirus, eventually becomes integrated in the host cell's genome. The retrovirus inserts its genome into a host chromosome, such that its genetic material becomes part of the genetic makeup of the infected cell, and is then replicated with the cell as the cell divides and multiplies. It is this characteristic which makes retroviruses especially persistent and immune to traditional anti-viral treatment. There is as yet no way to kill the retrovirus without killing the host cell. Thus, there is no proven cure, nor is there any proven effective vaccine or pharmacological agent against any retroviral disease.

Details of the life cycle and replication of retroviruses are discussed at length in Weiss et al, RNA Tumor Viruses, vols. 1 and 2 (Cold Springs Harbor Laboratory 1984), which is incorporated herein by reference in its entirety. FIG. 1(B) summarizes a model of a retrovirus life cycle. The life cycle of retroviruses is unique among viruses. The cycle begins when an infectious particle enters a host cell and releases two identical RNA molecules. These molecules are "reverse transcribed" by special viral enzymes to produce double-stranded DNA which circularizes and inserts into the host chromosome. FIG. 1(A) summarizes a model of the synthesis of double-strand DNA from viral RNA. The inserted DNA virus or "pro-virus" is structurally very similar to a normal host gene. It is transcribed to produce RNA, like any host gene. This RNA can then be processed in three ways: a) it can be directly translated into certain viral proteins, b) it can be processed and spliced, and then translated to produce other viral proteins, or c) it can be packaged, along with various viral proteins to make a newly infectious particle. In the case of HIV, the infectious particles continuously "bud off" the infected cells and bind to uninfected cells, beginning the cycle over again.

The retroviral particle which is the infectious agent contains in its interior two single-stranded positive-sense viral RNA molecules each between 7,000 to 11,000 nucleotide bases in length. These viral RNA's combine with certain viral proteins to form a viral core; the core being surrounded by a membrane. Imbedded in the membrane are viral glycoproteins which can specifically bind the viral particles to the appropriate host cell system. The viral core is assembled within the host cell and exits from the host cell, taking some of the host's membrane with it. Hence the membrane of the viral particle is derived directly from the host cell. The particle travels to an uninfected host cell, and due to the glycoprotein on its exterior binds to the new host cell and the life cycle repeats. Once the virus enters the cell, it is disassembled, releasing the two identical viral RNA molecules. These molecules are each composed of a sequence having specific functional regions making up the viruses "genomic structure".

The genome of any retrovirus is divided into three regions: the 5' terminus, the 3' terminus and a central region containing genes coding for proteins. The 5' terminus is further divided into four functional regions: the terminal redundancy (R), a unique sequence (U5), the primer binding site (PB− or PBS) and an untranslated sequence (L). The L region may contain a splice donor site for subgenomic mRNA. The 3' terminus is further divided into three functional regions: the primer-binding site for positive strand DNA synthesis (PB+ or PBS), a unique sequence (U3) and another copy of the terminal redundancy (R). The U5, U3 and R regions are sometimes collectively referred to as the Long Terminal Repeat (LTR) region. Components of the LTR region are involved in integration of the retroviral genome into the genome of its host. All retroviruses contain these highly conserved regions. These regions are further described by Weiss et al, supra, pp. 262-296.

The production of DNA from the infectious RNA occurs by a complex process called reverse transcription. The viral reverse transcriptase enzyme first complexes with a specific tRNA molecule supplied by the host cell. For example, in the case of the AIDS-related virus, it is lysine tRNA which complexes with the reverse transcriptase. The 3' end of the tRNA molecule remains free to hybridize with the primer binding site (PBS) of the retroviral genome. This is a sequence within the virus, which is complementary to the 5' end of the tRNA. Once the virus/enzyme/tRNA complex has been formed, the enzyme can make a new DNA molecule, using the RNA virus as a template, and using the tRNA as a "primer". As the process proceeds, the RNA of the resulting RNA/DNA complex is degraded, leaving single-stranded DNA. This process begins internally at the PBS site and proceeds to the 5' end of the RNA virus, where the process is stalled and regresses slightly, leaving a single-strand DNA "sticky end". At this point the enzyme/DNA complex has to "jump" to a new template at the 3' end of the virus. This jump, termed the first jump, is possible because the newly synthesized DNA is complementary to the other R region at the 3' end of the virus. After this jump, reverse transcription continues around to the point of the primer binding site.

After the "first jump" and while reverse transcription continues, second-strand DNA synthesis begins from the poly-purine site upstream of the U3 region. This DNA second-strand synthesis continues in the opposite direction from the first-strand DNA synthesis and proceeds through the primer binding site. The RNA primer molecule is consequently degraded, leaving a short residual region of second-strand DNA extending from the region of double-strand DNA. At this point the enzyme/DNA complex needs to make a "second jump" to a new template, this time jumping to the "sticky end" of the second strand DNA. This is possible because of complementation between the first and second strand DNA molecules in the region of the primer binding site. After hybridization of the complementary ends, reverse transcription can continue using the second-strand DNA as a template. This subsequently results in displacement of the first strand DNA, past the site of the first jump, up to the point where the second strand synthesis begins. Second-strand synthesis which was stalled at the PBS site prior to the second jump, can also continue after this jump, and proceeds to the 5' end of the first-strand DNA. The result of this process is a double-stranded DNA molecule with additional redundancies at both ends. Note that the DNA genomic structure differs from the RNA genomic structure in having a redundant U3 region added to the 5' end, and a redundant U5 region added to the 3' end. This occurs because the reverse translation process copies more than one full length of the RNA genome. Note also that this genomic structure now resembles a normal gene, with U3 being the promoter, with structural genes in the center, and a U5 tail.

The exact process of how the DNA virus inserts into host chromosomes is not known. It is known that the DNA virus first becomes a circle, and that this involves the short inverted repeat sequences at the ends of the virus. These inverted repeats may be involved in some form of DNA hybridization which brings the ends of the virus together, allowing circularization. Subsequently, insertion into the chromosome is generally assumed to be mediated by an enzyme which recognizes the splice site in the circle and directs insertion of a single copy of the virus into a random site within the host chromosome.

The transcription of viral DNA from the DNA pro-virus within a chromosome occurs in a manner similar to the transcription of any host gene. The U3 region functions as a polymerase II promoter and transcription begins at the beginning of the R region. The U3 promoter like eukaryotic promoters generally requires a transcriptional activator protein, which turns the promoter "on". Transcription proceeds through most of the pro-virus and is terminated at the end of the 3' R region. As a result, the transcript is a recreation of the smaller and infectious single-strand RNA genome. A poly-A tail is attached to the 3' end of this RNA and the 5' end is capped, making this molecule similar to normal host messenger RNA.

The RNA which is transcribed from DNA can be directly translated into protein, like any mRNA within the host. The GAG and Pol proteins are produced in this way and are subsequently cleaved into several smaller proteins involved in viral assembly and reproduction. In such a case, the 5' end of the RNA binds to a ribosome and protein translation beings at the first AUG codon initiation triplet of the coding sequence closest to the 5' end of the RNA molecule. Translation is terminated by one of the standard "stop" codons. Genes which are distant from the 5' end of the viral RNA cannot be directly translated because of the intervening genes, such as GAG. Such intervening genes can be removed by a splicing process which involves breaks at specific sites in the RNA molecule, and re-ligation of the appropriate pieces. In this case, the 5' end of the RNA molecule is unchanged, and binds to the ribosome as before, but now the first AUG codon where translation begins is not at the beginning of the GAG sequence, but at the beginning of some other coding sequence further downstream.

Some viral RNA is not translated into protein but rather is packaged into infectious viral particles. Such packaging involves the binding of certain viral proteins to specific sequences of the viral genome. For example, in the RSV viral system, it is part of the GAG sequence which is one of the parts of the genome which binds to and is recognized by such proteins and have been shown to be necessary for packaging of the RNA. The RNA which is packaged into viral particles does not appear to be reverse-transcription-competent until "maturation" of the particle, i.e., after it has existed away from the host cell.

All retroviruses, including HIV, once inserted into the host chromosome, must have their genes translated into viral proteins. If viral proteins are not abundant, the retrovirus cannot efficiently propagate to other cells and is not cytopathic to the infected host cell. Dayton et al, Cell, 44:941-947 (1986); Fisher al, Nature, 320: 367-371 (1986). Such proteins are not produced without the proper functioning of certain viral regulatory proteins. One of the key DNA/RNA-binding regulatory proteins for the retrovirus HIV is the TAT protein. Keegan et al, Science 231: 699-704 (1986). The TAT protein is essential to protein translation of HIV, and possibly also involved in RNA transcription. It is apparent that the TAT protein recognizes and binds to the nucleic acid sequence corresponding to the 5' end of the R region. A second activator gene ART has also been shown to be important in HIV translation. Sodroski et al, Nature, 321: 412-417 (1986). DNA/RNA binding of the previously described activator proteins is essential to HIV replication. Therefore, introducing genes into host cells, i.e., gene therapy for humans or germline transformation for animals, which will code for modified proteins of the retrovirus which compete or interfere with TAT or ART, will effectively block retrovirus replication.

Past research efforts have been predominantly confined to two traditional anti-retroviral approaches: immunological prevention and pharmacological therapy. Unfortunately, neither of these approaches appears to be very promising for control of retrovirus diseases. At best, an effective vaccination might reduce risk of infection in healthy individuals, but it would not be expected to cure an infected individual. Also, chemical repression of virus diseases has not generally been effective in eradicating any persistent virus, and certainly would not be expected to eradicate a retrovirus. Anti-viral chemicals tend to slow the progress of a virus and to bolster native defense mechanisms, but chemical treatments must be continuously applied and typically have undesirable side effects.

For these reasons, it is doubtful that any retroviral disease can be cured by the traditional anti-viral approaches. An alternative approach to inhibiting retrovirus replication is genetic inhibition by introducing nucleic acid constructs into host cells, i.e., gene therapy or germline transformation, which will confer cellular resistance by hybridization interference.

The inhibition or modulation of the various steps in the retroviral replication process by DNA or RNA which will hybridize and block viral sequences has been termed "hybridization interference". Green et al, ANN. REV. Biochem., 55:569-97 (1987), which is incorporated herein by reference. There are essential steps in retrovirus replication which require nucleic acid hybridization, Gilboa et al, Cell, 6: 93-100 (1979). If any of these replication steps are blocked by pre-binding of the essential sites in the retrovirus genome; or binding of proteins or other cellular constituents in the retrovirus genome, to molecules coded for by genetically engineered nucleic acid sequences in the host cell the retrovirus replication process can not proceed. Note, that "Hybridization Interference" has also been referred to as an "Anti-sense approach". Green et al, ANN. REV. Biochem., 55:569-97 (1987). However, an ambiguity exists in that "sense" and "anti-sense" only apply to sequences coding for proteins, and nucleic acid constructs are disclosed herein which target retrovirus sequences not coding for proteins. Consequently, as used throughout the specification and appended claims, "Hybridization Interference" or "Anti-sense RNA" should refer to the use of RNA or DNA to bind with nucleic acid, protein or other cellular constituents to inhibit retrovirus replication.

The effectiveness of the anti-sense RNA approach has been demonstrated in several model viral systems. It was demonstrated in the SP bacteriophage system that certain messenger-RNA-interfering complementary RNA (micRNA) can have very significant anti-viral effects, as seen by reduced plaque number and plaque size, Coleman et al, Nature, 315: 601-603 (1985).

In addition, it has been suggested that the replication and cell transformation of the Rous Sarcoma Virus (RSV) was inhibited by a specific synthetic tridecamer oligodeoxynucleotide, Zamecnik and Stephenson, Proc. Natl. Acad. Sci., 75: pp. 280-2BB (1978). The synthetic complementary tridecamer was introduced extracellularly into the cytoplasm of chick embryo fibroblast cells infected with RSV virus, thereby blocking RSV replication by hybridization competition. However the tridecamer was not incorporated into the host genome or any other genetic vehicle, such that neither the sequence, nor an equivalent coding sequence, would replicate in the cell. This is a chemotherapeutic approach to inhibiting virus replication, and not gene therapy.

Another publication has shown that synthetic exogenous oligodeoxynucleotides complementary to regions of the HIV genome inhibit virus replication and gene expression in cultured cells. Sequences of exogenous synthetic oligodeoxynucleotides 12, 20, and 26 nucleotides in length were tested on infected cells, Zamecnik et al, Proc. Natl. Acad. Sci., 83:4143-4146 (1986). Again, the oligodeoxynucleotides are exogenous and were not incorporated into the host genome or another vehicle which would provide for the replication or maintenance of the tridecamer.

Finally, the anti-sense RNA-mediated inhibition on the replication of avian retrovirus in cultured cells was suggested using natural gene sequences derived from the neomycin resistant gene of the bacterial transposable element Tn5, To et al, Molecular and Cellular Biology, vol. 6, No. 12, pp. 4758-4762 (1986).

In the field of human medicine, altering the genotype of the host has not been a desirable method of fighting infectious disease. However, it is now believed that gene therapy will be possible in the relative future, Anderson, Science, 226:401-409 (1984). As a result, application of the anti-sense RNA approach within the field of medicine may be possible. Presently available gene therapy techniques are only effective for the genetic modification of bone marrow and blood cells. Because of this limitation, the projected use of gene therapy has generally been assumed limited to the correction of rare hereditary gene defects where such defects center in bone marrow or blood cells. Despite these limitations there are certain pathogens of the blood for which conventional defenses appear inadequate, and where the use of anti-sense RNA inhibition might be feasible. Many of the cells that are infected by retroviruses are derived from hematopoetic stem cells. If these stem cells can be altered by the incorporation of genes or other nucleic acid sequences which will synthesize RNA molecules that are antagonistic to virus propagation, an efficient method to both effectively prevent and to treat these retroviral diseases will be apparent. Further, if the expression of the RNA inhibiting genes can be regulated in the desired cells, it has application to other genetic diseases.

It would therefore be desirable to provide methods and compositions for producing RNA which is complementary or corresponding to an essential retroviral hybridization site within the retrovirus genome selected from the group consisting of the LTR region, the U5 region, the U3 region, the R region, the PBS region, the AUG start codon regions, the polyP region, RNA splice sites, the leader region, the TAT splice site, the ART splice site and the cap site which would be effective to inhibit retroviral replication.

Another objective is to provide methods and compositions for expression in a host cell system of a synthetic double-strand DNA fragment coding for an RNA fragment complementary or corresponding to an essential retroviral hybridization site within the retrovirus genome selected from the group consisting of the LTR region, the U5 region the U3 region, the R region, the PBS region, the AUG start codon regions, the polyP region, RNA splice sites, the leader region, the TAT splice site, the ART splice site and the cap site, without adverse side effects to the host cell resulting from such gene expression.

SUMMARY OF THE INVENTION

In accordance with the present invention, a method of conferring genetic resistance to retroviral infection upon a host cell is disclosed. The method involves transforming the host cell with a vector comprising a polynucleotide directing transcription within the host cell of RNA which (a) is complementary or corresponding to a nucleic acid sequence within one or more regions within the genome of the retrovirus selected from the group consisting of the LTR region, the U5 region, the U3 region, the R region, the PBS region, the AUG start codon regions, the polyP region, RNA splice sites, the leader region, the TAT splice site, the ART splice site and the cap site, and (b) is effective to inhibit replication of the retrovirus when the host cell is infected. The method also involves transforming the host cell with a vector comprising a polynucleotide directing transcription within the host cell of RNA which corresponds to sequences which represent a small portion of the RNA genome, which can bind to a viral protein.

Cells upon which resistance to infection is to be conferred, are transformed with a polynucleotide via a vector. "Transformation" or "transformed", as those terms are used throughout this specification and the appended claims, is intended to cover any and all methods of introducing a polynucleotide and its other attendant nucleic acid sequences, if any, into a cell. Those terms are not intended to be limited to the process of "true" transformation which is known to those in the art. Methods included within those terms include, without limitation, transformation, transfection, micrionjection, $CaPO_4$ precipitation, electroporation, targeted liposomes, particle-gun bombardment, electro-fusion, and infection.

The polynucleotide used to transform the cell upon which resistance is conferred can be either single- or double-stranded RNA or DNA. The polynucleotide "directs" transcription of a specific RNA molecule in the cell. A polynucleotide can "direct" such transcription by being directly transcribed (e.g., double-stranded DNA in a plasmid) or by coding for nucleic acid which is later transcribed to produce the RNA molecule (i.e., serves as a template for RNA or DNA which is either transcribed or serves as a further template for nucleic acid which is transcribed; e.g., single-stranded RNA in a virus which is transcribed to produce DNA which is incorporated into the host cell genome and in turn transcribed). In addition to the sequence specifically directing the transcription of the operative RNA, the polynucleotide can include a promoter and/or a terminator that will regulate the transcription of the polynucleotide. The polynucleotide may be derived from a naturally-occurring sequence or synthesized in vitro.

Used herein, a RNA molecule is complementary ("anti-sense") a given nucleic acid sequence if it will effectively bind or hybridize to any portion of the given nucleic acid sequence, wherein the nucleic acid sequence is an essential hybridization site within the retroviral genome, so as to inhibit a process involved in retroviral replication. Similarly, an RNA molecule is "corresponding" to a certain nucleic acid sequence if it will bind to any portion of a nucleic acid which is complementary, as defined above, to the certain nucleic acid sequence so as to produce the inhibition of retroviral replication. No specific degree or percentage of complementarity (as the term is traditionally used in the art), base-to-base pairing, homology (as that term is traditionally used in the art), or base-to-base comparison is required.

The RNA directed by the polynucleotide is complementary or corresponding to "one or more" of certain regions within the retroviral genome. In other words, the RNA may overlap between several regions or portions of regions; or the polynucleotide can direct transcription of RNA at several different sites.

The RNA directed by the polynucleotide must be effective to inhibit the replication of the retrovirus. Inhibition can be exhibited by any decrease in the extent or rate of insertion and proliferation of the retrovirus. Replication need not be completely stopped to constitute "inhibition."

The polynucleotide is transformed via a vector. Any known vectors, including without limitation, viral vectors, retroviral vectors and plasmids, may be used. Preferably the vector is a plasmid. The vector can include a promoter and/or a terminator for regulation of the polynucleotide. The final construct (vector and polynucleotide) can include one or more promoters and/or terminators including those made part of the polynucleotide as described above. The vector can also include a selectable marker for detection and isolation of successfully transformed cells including without limitation antibiotic resistance to neomycin, ampicillin, or xanthine.

The present invention is applicable to any retrovirus, including without limitation a human T-cell lymphotrophic virus, a human immunodeficiency virus, a lymphadenopathic virus, a leukemia virus, a sarcoma virus, and a virus causing a lymphotrophic disease. Such viruses include without limitation HIV, feline leukemia virus ("FeLV"), HTLV-1, HTLV-2, murine leukemia virus and avian leukemia virus. Preferably the retrovirus is HIV, HTLV-1, FeLV, or FIV.

Nucleic acid constructs, including a polynucleotide as previously described, are also disclosed. The construct can include a vector as previously described.

Resistance to retroviral infection is conferred to host cells by hybridization interference, or by modified viral proteins. "Hybridizaton" is the coming together of single-stranded nucleic acid chains with their complementary nucleotide sequences into double-stranded nucleic acid chains when subjected to hybridizing conditions. "Hybridization Interference" is the inhibition of viral replication by "hybridization" of interfering nucleic acid sequences.

Cells upon which resistance to infection has been conferred by the above-described methods and their progeny are also disclosed. The progeny of the originally transformed cells "contain a sequence which is descendant from" the polynucleotide previously described. A sequence is "descendant" if its history can be traced back to the polynucleotide. The descendant sequence does not have to be an exact copy of the polynucleotide; it need only maintain the function of the polynucleotide in the inhibition process. In essence, a "descendant sequence" must "correspond" (as defined above) to the polynucleotide. The descendant sequence can have been deleted, inserted, mutated, inverted or altered by other means as long as its functional identity with the polynucleotide is maintained.

RNA molecules directed by the polynucleotide are also disclosed. Such molecules are (a) complementary or corresponding to a nucleic acid sequence within the genome of a retrovirus, and (b) being effective to inhibit replication of the retrovirus.

A method of treatment is disclosed in which cells, upon which resistance to infection has been conferred, are introduced into a patient.

BRIEF DESCRIPTION OF THE FIGURES

FIG. 1A is a schematic representation summarizing a model of the synthesis of double-strand DNA from viral RNA.

FIG. 2 is the LTR gene structure for the HIV genome.

FIG. 3 is the LTR gene structure for the HTLV-I genome.

FIG. 4 is the LTR gene structure for the FeLV genome.

FIG. 5 is Table 1 which lists sequences targeted against HIV which are exemplary of polynucelotides employed in practicing the present invention.

FIG. 6 is the anti-R gene structure for the retrovirus HTLV-I.

FIG. 7 is the anti-R gene structure for the retrovirus FeLV.

FIG. 8 is the anti-R gene structure for the retrovirus HIV.

FIG. 9 is the anti-PBS gene structure for the retrovirus

FIG. 10 is the anti-PBS gene structure for the retrovirus HTLV-1.

FIG. 11 is the anti-PBS gene structure for the retrovirus HIV.

FIG. 12 is the anti-AUG and anti-S.D. gene structure for the retrovirus FeLV.

FIG. 13 is the anti-AUG and anti-S.D. gene structure for the retrovirus HTLV-1.

FIG. 14 is the anti-AUG, an anti-S.D. gene structure for the retrovirus HIV.

FIG. 22 illustrates multiple polynucleotide constructs for the retrovirus HIV in accordance with the present invention.

FIG. 23 illustrates multiple polynucleotide constructs for the retrovirus FeLV in accordance with the present invention.

FIG. 24 illustrates multiple polynucleotide constructs for the retrovirus HTLV I in accordance with the present invention.

DETAILED DESCRIPTION OF THE INVENTION

Figure 1B:
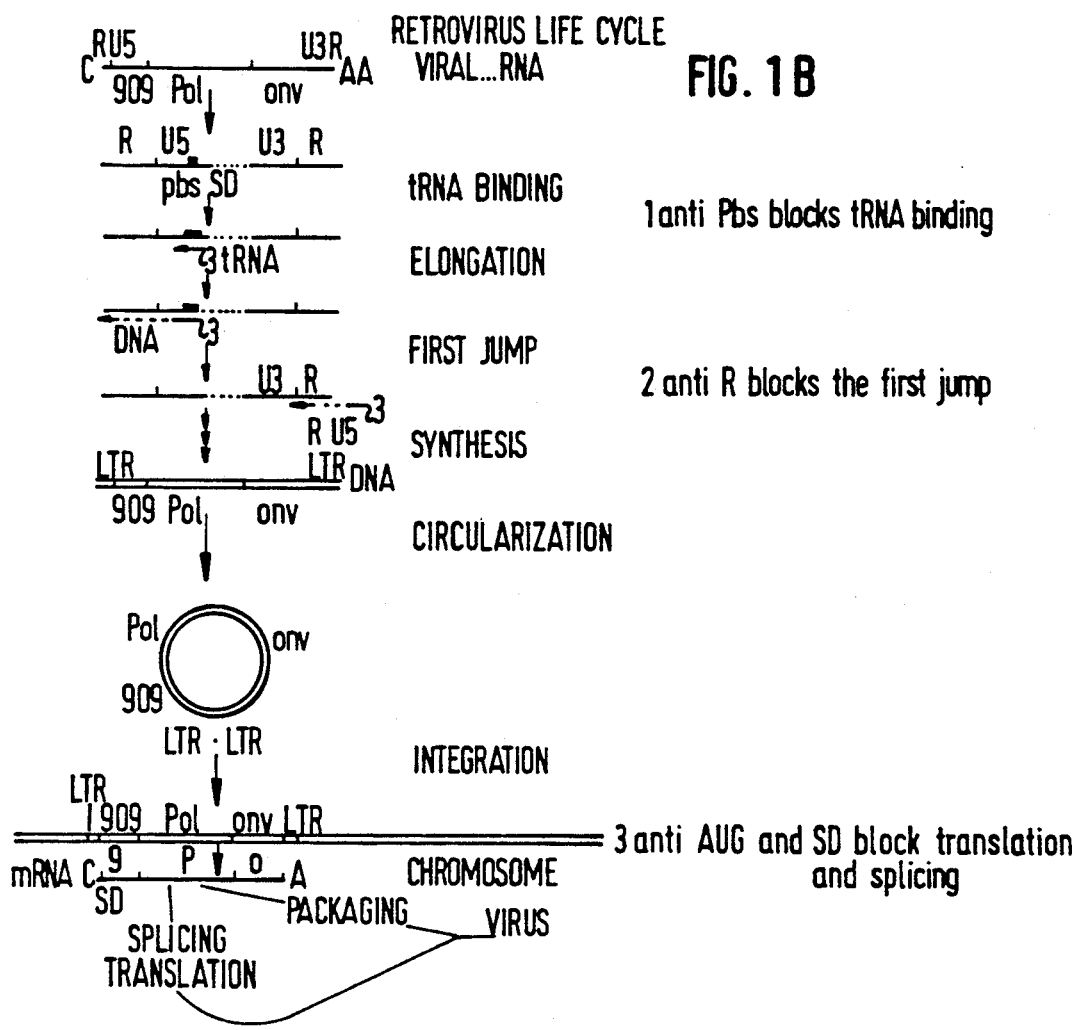
FIG. 1B is a schematic representation showing a general overview of a retrovirus lifecycle.

Many of the procedures useful for practicing the present invention, whether or not described herein in detail, are well known to those skilled in the art of Recombinant DNA technology. A detailed description of many of such procedures can be found in Maniatis et al, *Molecular Cloning: A Laboratory Manual*, Cold Spring Harbor Laboratory, Cold Spring Harbor, NY, (1982).

The present invention specifically involves the inhibition of retroviral replication by RNA complementary or corresponding to essential replication and assembly sites in the retrovirus genome or proteins. In the following examples, the methods of the present invention are applied to HIV, HTLV-1, and FeLV viruses for purposes of illustration of the invention taught herein and are not limited thereto. The nucleic acid sequences of the Long Terminal Repeat region of HIV, HTLV-1 and FeLV are shown in FIGS. 2, 3 and 4, respectively. Table 1 lists several sequences which are exemplary of the polynucleotides employed in practicing the present invention. (See FIG. 5) Use of these sequences is not limited to the HIV virus but can apply in accordance with the methods described herein to all retroviruses, although some changes in specific bases within the polynucleotide may be required. The genetic code is degenerate and redundant, that is, numerous substitutions, deletions, inversions or insertions of nucleotides will code for the same end product, i.e., protein. Consequently, it will be apparent that any changes or modifications to a given polynucleotide that produce a new polynucleotide that either retains the ability to code for the same end product i.e., protein, or retains sufficient functional sequence identity to hybridize to targeted nucleic acid sequences within the retroviral genome so as to inhibit retroviral replication, are functional equivalents of specific sequences disclosed herein.

The term "nucleic acid construct" as used herein, refers to one or more nucleotide sequences (polynucleotides or genes) that are inserted into one of the vectors chosen from the group of vectors including a virus, retrovirus, or plasmid. The polynucleotide sequences described herein are preferably DNA, but could include RNA or a combination thereof, and are integrated into the appropriate vector by ligation or other similar techniques. With reference to Table 1, there are listed sequences which are illustrative of the polynucleotides of the nucleic acid constructs which are inserted into the appropriate vector.

EXAMPLE 1

Preferred Embodiment of the Invention

The preferred novel nucleic acid construct in accordance with the present invention is a double-stranded DNA oligonucleotide sequence operatively linked to a Pol III promoter and terminator. The nucleic acid construct can be transcribed resulting RNA molecule complementary (anti-sense) or corresponding to a nucleic acid segment within the retrovirus genome essential to retrovirus replication including the LTR, the AUG start codon regions, RNA splice sites, the U5 region, the U3 region, the PBS region, the cap site, the TAT splice site, the ART splice site, the leader region and the polyP region.

Unmodified polynucleotides were synthesized on an automated DNA synthesizer (Biosearch, San Rafael, California) using standard phosphoramidite chemistry, Gait, M. J. ed., *Oligonucleotide Synthesis*, IRL Oxford, Biosearch, Inc., Instruction Manual Model 8600, San Rafael, Calif., (1984). Deblocking of the support-bound 5'-OMT group is removed with dichloroacetic acid to generate free 5'-OH for coupling. The 5'-OH is treated with a mixture of amidite and activator. This coupling results in a formation of a new phosphorus-oxygen bond which increases the length of the polynucleotide by one base unit. Because the dichloroacetic acid used in the deblocking step can break the phosphorous (III)-oxygen bond, it is necessary to oxidize the phosphorous (III) to a stable phosphorus (V) oxidation state.

Iodine is used in this oxidation procedure. The unreacted 5' OH groups are capped to prevent further reaction. Ammonia hydroxide cleaves the synthesized polynucleotide from the support. The cyanoethyl groups on the phosphorus, the benzoyl and isobutyl groups on the primary amino groups of the bases, are removed from the DNA fragment by treating the collected ammonium hydroxide solution at 50° C for 5 hours. The polynucleotides were purified using 5% polyacrylamide gel electrophoresis, Maxam et al, P.N.A.S., 74: 560–564 (1977). The novel nucleic acid constructs have a preferred range from about 25 to 200 bases in length. The constructs were assembled from polynucleotides 30 to 45 bases in length. The short strand polynucleotides were constructed with sticky ends and complementary to each other so the complementary fragments would hybridize to form duplexes. The duplexes were then ligated together at the sticky ends using a ligation mixture of T4 DNA ligase, 10x ligase buffer, 10 mM ATP, and distilled water in a water bath at 50° C. to form a double-stranded DNA fragment.

Polynucleotides complementary to the R region (hereinafter Anti-R), the primer binding region (hereinafter Anti-PBS); the splice sites (herein after Anti-S), the cap site (hereinafter Anti-cap) and the first AUG start codon region (hereinafter Anti-AUG) in the Long Terminal Repeat region of the retroviruses HIV and FeLV were synthesized. Polynucleotides complementary to the above sites will also be synthesized for HTLV-1. Note that the Anti-PBS constructs are identical for HTLV-1 and FeLV since their genomic sequences share sequence identity. The sequences of these polynucleotides are shown in FIGS. 6–14. To derive the specific antisense strand it was necessary to start with the RNA sequence of the desired retrovirus. Then, the corresponding DNA strand is designed from the RNA strand by replacing the Uracil nucleotides with Thymine. To obtain the antisense strand, the DNA sequence is inverted in order and the complementary sequence is designed. This yields the exact nucleotide sequence to be synthesized. The polynucleotide constructs are of sufficient length to insure stability and prevent degradation by host cell enzymes. But, the length associated with the constructs herein reduces the problem of the formation of tertiary structures associated with long strand polynucleotides which fold or "hairpin" thus preventing binding of the fragments to the retrovirus nucleic acid fragment.

The nucleic acid constructs were further constructed with flanking restriction sites at the 5' and 3' ends. Each polynucleotide was synthesized with a HindIII and a BamHI site at either end to allow insertion in both orientations. The nucleotide sequence for the HindIII site is "AAGCTT"; the nucleotide sequence for the BamHI site is "GGATCC".

A vector was used to introduce the nucleic acid constructs into a cell. "Vector" specifically refers to a flanking nucleic acid sequence which will allow the synthetic polynucleotide to be introduced into a cell and then either inserted into a chromosome or replicated autonomously. Certain vectors, e.g., plasmids, may also be used as a means to amplify the constructs of the present invention. The plasmids pRSVneo, pSV2gpt, pSV2neo, pUC19, and pRSVgpt were used as vectors for the preferred constructs of the present invention. Plasmids are circular pieces of DNA. They generally have a bacterial origin of replication and a selectable marker gene appropriate for amplification within a bacterial host such as *E. coli*. Plasmid pRSVneo has a marker gene which confers resistance to ampicillin. Plasmid pRSVgpt has a marker gene which confers resistance to xanthine. Other vectors, including without limitation other plasmids, viruses and retroviruses can alternatively be used in practicing the present invention. The plasmids used herein were selected because they are well characterized, have good dominant selective markers when incorporated into a cell, and the restriction endonucleases HindIII and BamHI only cut once making it relatively easy to clone the novel nucleic acid constructs of the present invention into the plasmids.

The selected plasmids pRSVneo, pSV2gpt, pSV2neo, pUC19, and pRSVgpt were each linearized by digestion with conventional restriction endonucleases BamHI and HindIII respectively. The restriction enzymes were added to plasmids at conventional concentrations and temperature and with buffers as recommended by the manufacturer, Bethesda Research Lab. The digestion mixture consisted of plasmid DNA, TE buffer (pH=8), 2X restriction buffer, and the restriction enzyme. The mixture was incubated in a 37° water bath for 3 hours. The digest was then applied to a 1% preparative agarose gel and electrophoresed for 1 hour at 100 volts to separate the cut plasmid fragments from the uncut supercoiled plasmids according to the standard procedure described in Maniatis et al, *Molecular Cloning,* (1982). The linearized plasmids were then ligated together at the restriction endonuclease sites HindIII and BamHI respectively using a ligation mixture of T4 DNA ligase, 10x ligase buffer, 10 mM ATP, and distilled water in a water bath at 50° C. to form a re-circularized double-stranded plasmid comprising the synthesized nucleic acid construct.

Figure 16:
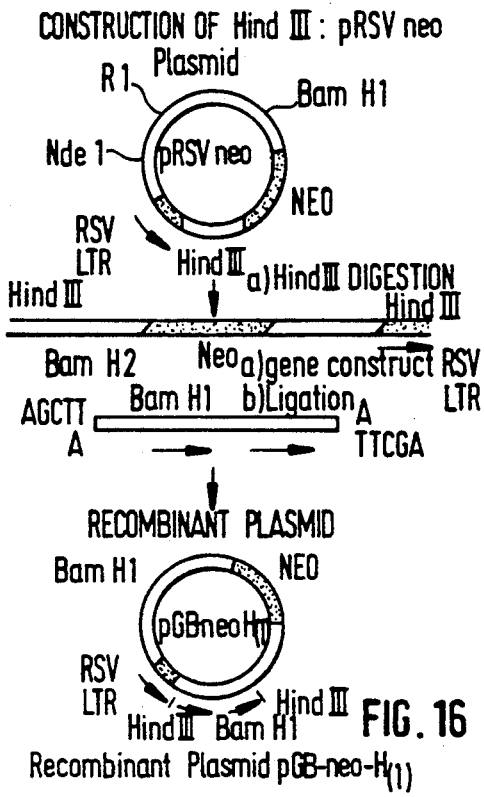
FIG. 16 is the construction of recombinant plasmid pGB-neo-H(1) in the same transcription orientation relative to the plasmid promoter.
Figure 17:
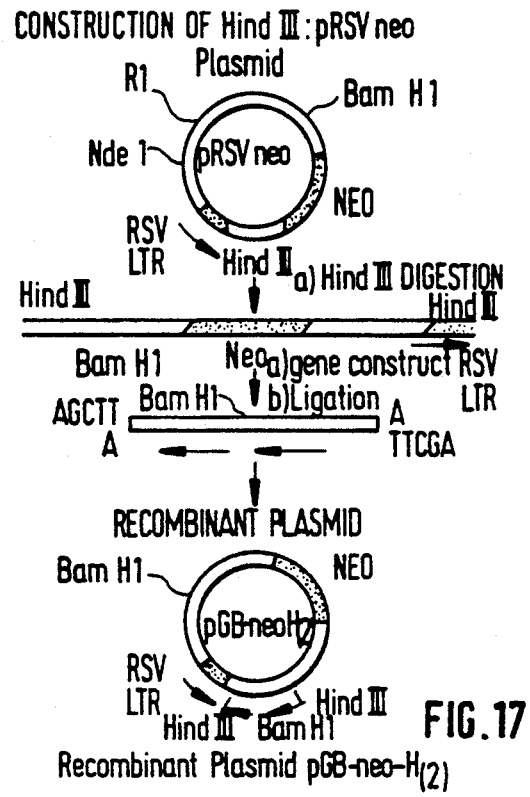
FIG. 17 is the construction of recombinant plasmid pGB-neo-G(2) in the opposite transcription orientation relative to the plasmid promoter.
Figure 18:
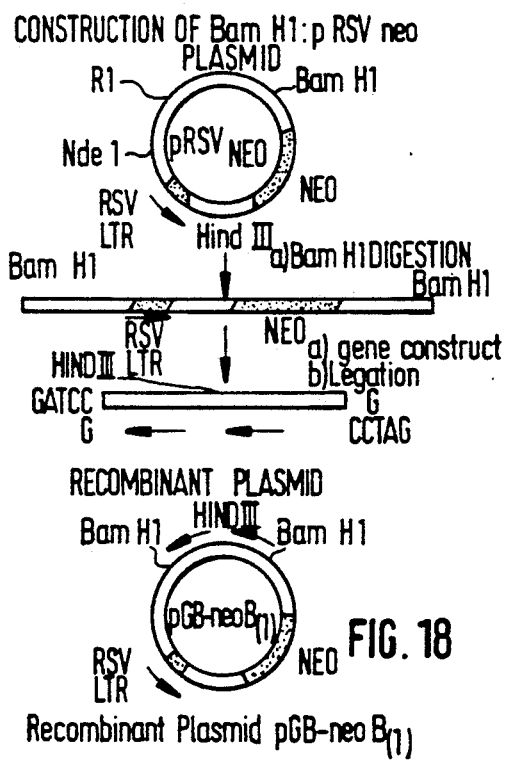
FIG. 18 is the construction of recombinant plasmid BamHI: pRSVneo in the same transcription orientation relative to the plasmid promoter.
Figure 19:
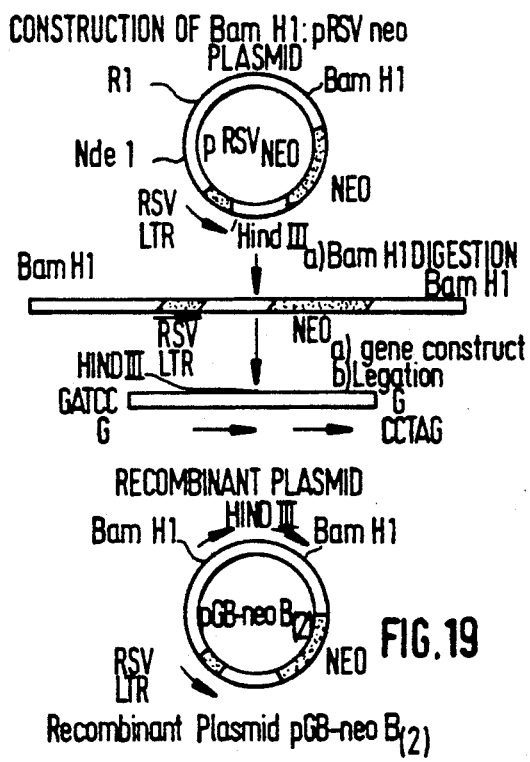
FIG. 19 is the construction of recombinant plasmid BamHI: pRSVneo is the opposite orientation relative to the plasmid promoter.
Figure 20:
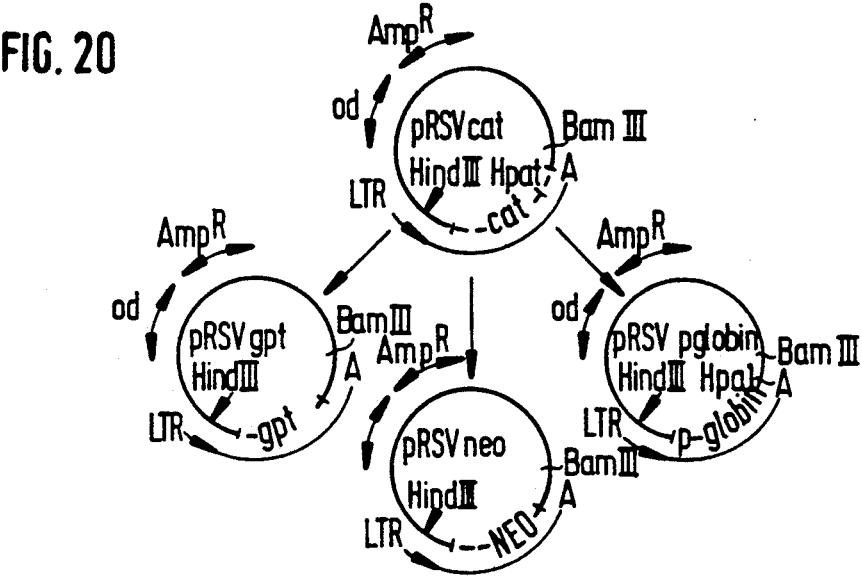
FIG. 20 is a schematic illustration of the RSV vector family.
Figure 21:
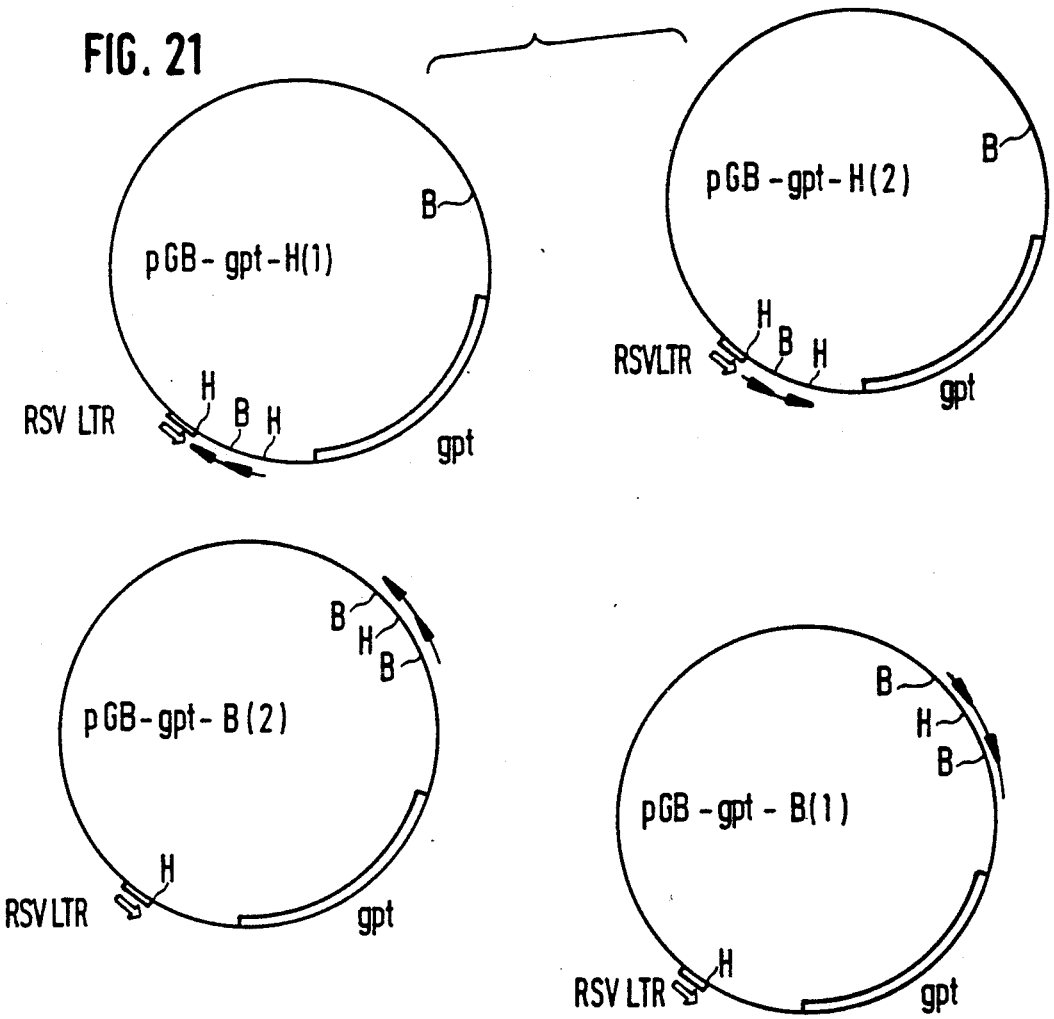
FIG. 21 is a schematic illustration of recombinant plasmids pRSVgpt including the polynucleotide constructs of the present invention in both orientations relative to the plasmid promoter.

Recombinant plasmid designations are as follows: "p" signifies plasmid, "GB" signifies the plasmid was constructed by Greatbatch GenAid, and "neo" signifies the selectable marker in the RSV vector family. In constructing recombinant PRSV neo vectors, one or more polynucleotides comprising a nucleic acid construct was inserted at either the HindIII restriction site (hereinafter HindIII construct) or the BamHI restriction site (hereinafter BamHI construct). Plasmids where the nucleic acid construct was inserted at the HindIII site would carry "H" in their designation i.e. pGB-neo-H, while those inserted at the BamHI site are designated with a "B", pGB-neo-B. Each nucleic acid sequence was inserted in two different orientations with respect to the plasmid promoter, in each restriction site (either HindIII or BamHI). That is, FIG. 16 illustrates insertion of a nucleic acid sequence into the HindIII site in the same orientation as the plasmid promoter and therefore designated pGB-neo-H1. FIG. 17 shows insertion into the HindIII site in the opposite orientation to the plasmid promoter and therefore is designated pGB-neo-H2. Similarly, insertion of a nucleic acid construct into the BamHI site in the same orientation to the plasmid promoter is designated pGB-neo-B1 (FIG. 18) and in the opposite orientation, pGB-neo-B2 (FIG. 19). Refer to FIG. 20 illustrating the RSV vector family. The figures show two illustrations for each restriction site because the nucleic acid constructs were cloned into the plasmids in both transcription orientations relative to the plasmid RSV promoter. The BamHI construct for FeLV was inserted at nucleotides 3393 through 3678 in the pRSVneo plasmid. The HindIII construct for FeLV was inserted at nucleotide 5736 through 5921 in the pRSVneo plasmid. The BamHI construct for HIV was inserted into the plasmid pRSVgpt at nucleotides 3393 through 3733. The HindIII construct for HIV was inserted into the plasmid pRSVgpt at nucleotides 5736 through 6076. The difference between plasmid constructs pRSVgpt and pRSVneo is pRSVgpt has the gpt gene instead of the neo gene as shown in FIG. 21. The pRSVgpt recombinant plasmids are designated in the same manner as the pRSVneo plasmids except neo is replaced with gpt.

E. coli cells were transformed with the modified plasmids comprising the nucleic acid constructs for the purpose of amplifying the plasmids. Cells of E. coli HB101, to be transformed with the plasmids pRSVneo and pRSVgpt were grown in L broth at 37° C. with shaking to an OD550=0.5 ($5 \times 10^7$ cells/ml). 3 ml of cells were chilled on ice for 10 minutes and harvested by centrifugation in a Sorvall rotor for 5 minutes at 4,000 rpm at 4° C. Cells were resuspended in ½ original volume in solution of 50 mM CaCl$_2$ and 10 mM Tris-Cl (pH 8.0), incubated on ice for 15 minutes, centrifuged at 4,000 rpm for 5 minutes at 4° C. The cells were resuspended in 1/15 of original volume in solution of 50 mM CaCl$_2$ and 10 mM Tris. Cl (pH 8.0). 0.2 ml aliquots were dispensed into chilled tubes, and stored at 4° C. for 12-24 hours. 0.4 mg of plasmid DNA in ligation buffer were added to the cells. The cells were then incubated on ice for 30 minutes, and transferred to a waterbath at 42° C. for 2 minutes. 1.0 ml of L broth were added to each tube and incubated at 37° C. for 30 minutes.

The transformed cells were selected for by spreading the cells on enriched plates containing 2xYT medium, 0.15% Bacto-agar (Difco) and 20 mg/ml ampicillin for pRSVneo and xanthine for pRSVgpt. The transformed E. coli HB101 cells carrying the respective plasmids were amplified by growing the cells with shaking at 37° C. in 1 liter LB medium to an OD600 of 0.6. 2.5 ml of chloramphenicol (34 mg/ml in ethanol) were added, and vigorous shaking applied for 12-16 hours. To isolate the amplified plasmid DNA, one or more liters of cells of E. coli HB101 were harvested by centrifugation at 4,000 rpm for 10 minutes in a Sorvall rotor and then resuspended in 10 ml of a solution containing 50 mM glucose, 25 mM Tris-Cl (pH 8), 10 mM EDTA, 5 mg/ml lysozyme. The cells were left at room temperature for 5 minutes. 20 ml of Solution II containing 12N NaOH, 1% SDS were added to the cells and then incubated on ice for 10 minutes. 15 ml of a cold solution of 5M potassium acetate (pH 4.8) were added to the cell solution, mixed by inversion and incubated on ice for 10 minutes. The cell lysis was centrifuged for 20 minutes at 4° C., at 20,000 rpm in a Beckman centrifuge. The plasmid DNA in the supernatant was precipitated with 0.6 volumes of isopropanol at room temperature for 15 minutes. The plasmid DNA was recovered by centrifugation in a Sorvall rotor at 12,000 rpm for 30 minutes at room temperatures. The pellet was washed with 70% ethanol at room temperature, dryed, and resuspended in total volume 8 ml of TE (pH 8.0). To purify the isolated plasmid DNA, the total volume of isolated plasmid DNA was measured. For every ml of plasmid DNA exactly 1 gram of solid cesium chloride was added, and mixed gently until the salt dissolved. To it was added 0.8 ml of ethidium bromide (10 mg/ml in H$_2$O) solution for every 10 ml of cesium chloride solution, mixed to yield a final density of 1.55 g/ml, and final concentration of ethidium bromide of approximately 600 ug/ml. The cesium chloride solution was transferred to tubes suitable for centrifugation in a Beckman Type 50 or Type 65 rotor. The remainder of the tube was filled with paraffin oil and then contrifuged at 45,000 rpm for 36 hours at 20° C. Two bands of DNA were visible, an upper band consisting of linear bacterial DNA and circular plasmid DNA, a lower band consisting of closed circular plasmid DNA. The lower band of plasmid DNA was collected by side puncture with a #21 hypodermic needle. The ethidium bromide was removed by adding equal volumes of 1-butanol saturated with water, then mixed and centrifuged at 1,500 rpm for 3 minutes at room temperature. The aqueous lower phase was transferred to a clean tube and the above step repeated until the pink color disappeared. The aqueous phase was dialyzed with TE (pH 8.0). The preceding procedures are applicable to any nucleic acid construct cloned into any suitable plasmid in accordance with the methods taught herein.

An effective method of delivering the vector DNA into the target cell is required if high efficiency transformation is to be achieved. Transformation of potential host cells was carried out by CaPO$_4$ precipitation by standard procedures in the state of the art. Other suitable transformation methods are applicable herein and can be substituted. See Ausubel et al, *Current Protocols in Molecular Biology*, (1987), which is incorporated herein by reference. For example, electroporation can be expected to increase plasmid transformation efficiencies. Transformation of HUT-78 cells i.e., a suitable host cell system for HIV, was accomplished using a pRSVneo plasmid (without nucleic acid constructs) using electroporation at 1000 V (2000 v/cm) and a 14 mf capacitor, which gave a pulse length of 1.9 ms. This is an energy of ½ CE2 or 7 joules. The HUT-78 cells were challenged with neomycin which demonstrated that the plasmid had indeed been transformed and expressed. In addition, an alternative method for delivering plasmid DNA into target cells which is believed to be particularly well suited to the treating of AIDS patients involves a) encapsulating plasmid DNA into liposomes, using established methods, b) binding commercially available antibodies to the surface of the liposomes which specifically bind to T4 cells, and c) injecting these liposomes into the blood stream of the AIDS patient. The antibody-targeted liposomes will bind to T4 cells, and will continually be absorbed by the cell, leading to transformation. Subsequently, transformed T4 cells will ave a selective advantage over non-transformed cells, due to their immunity to the HIV virus. Such resistant cells will multiply as susceptible cells are killed off by the virus. This selection process can be enhanced by use of selective agents (i.e., antibiotics) favoring the transformed cells. Also, irradiation of the patient prior to injection of targeted liposomes could further reduce the number of infected T4 cells. This technique is well known to those skilled in the art of treatment of infant leukemias.

Figure 33:
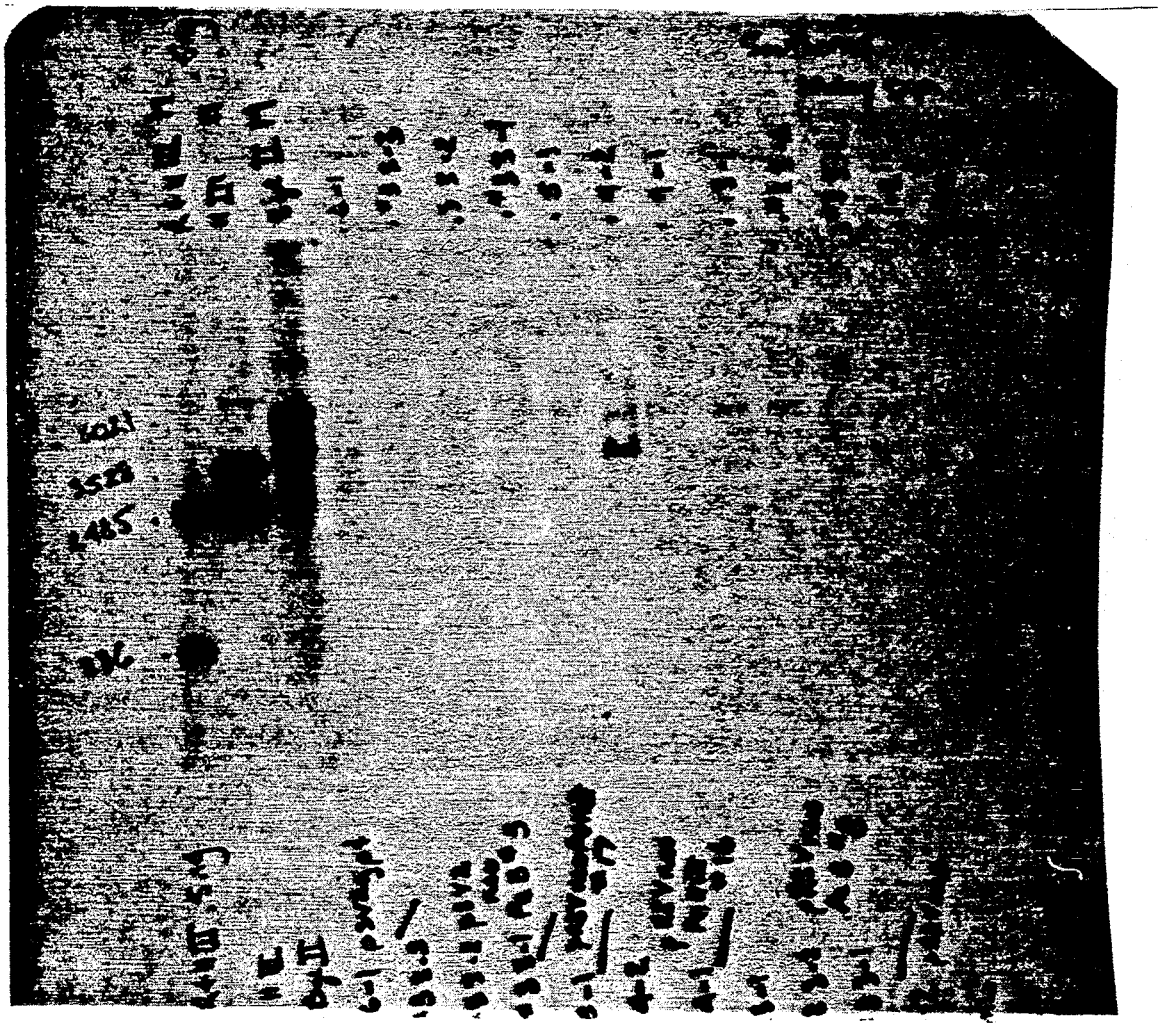
FIGS. 33 and 34 are Southern blot-hybridization results using ribo probes Neo and Bam respectively.
Figure 34:
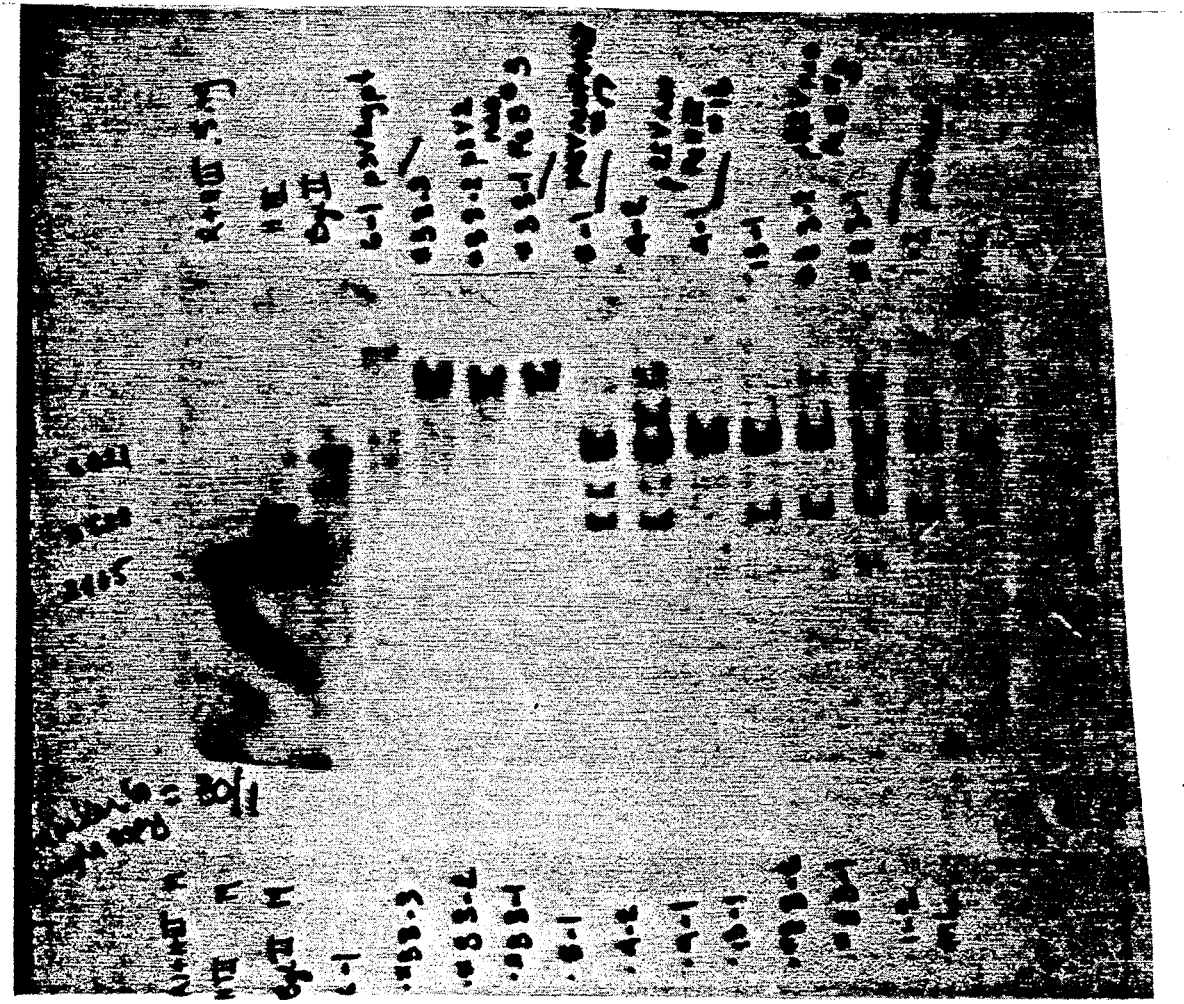

In accordance with the CaPO$_4$ precipitation procedure, a DNA slurry was prepared with 1 ml HBS buffer, 10 ml DNA sample (1 ug/ul), 18-25 ul 2.5 M CaCl$_2$, added one drop at a time and vortexed. The remaining CaCl$_2$ was added and let stand at room temperature for 5 minutes. A media containing DME and mink lung cells was aspirated from dishes, and washed with HBS buffer. Then 500 ul DNA slurry sample and 4ml of media containing the mink lung cells were added to each dish and incubated for 4 hours at 37° C. The media was removed and 2 ml of 15% glycerol was added. The media was incubated for 3 minutes at 37° C. and then the glycerol was removed by aspirating. 4 ml of fresh media was added and the media was incubated at 37° C. for 48 hours. The transformed cells were selected by spreading the cells on a selective media depending on the particular plasmid i.e., ampicillin or xanthine, and incubated for two days at 37° C. G418 was the selective media for the ampicillin resistant plasmid pRSVneo. HAT media was the selective media for the xanthine resistant plasmid pRSVgpt. The transformed cells were the colonies that grew on the selective media after several weeks. Northern blot-hybridization analysis and Southern blot-hybridization analysis were used to verify the presence of high levels of RNA or DNA in the transformed cells. The probes for the Southerns and Northerns were constructed using ribo probes and in-vitro transcription with T7 RNA polymerase. FIGS. 33 and 34 show representative Southern blot hybridization analysis to verify the presence of the plasmid comprising the nucleic acid construct within the transformed mink lung cells. FIG. 33 shows a blot analysis probing with ribo probe neo. This test result indicates that the plasmid was taken up by the mink lung cells during transformation and expressed by the cells. Plasmids pRSVneo:FeLV BamHI, nos. B, 3-1, 8, 3-2 and 13-1 in rows 11, 12 and 13 respectively show bands measuring about 2485 kb indicating the presence of the plasmid. FIG. 34 shows a blot analysis probing with ribo probe BamHI. This test result indicates that the nucleic acid construct was present in the plasmid taken up by the mink lung cells during transformation. Plasmids pRSVneo:FeLV BamHI, nos. 13-1, B, 3-2 and in rows 11 and 12 respectively show bands measuring about 6021 kb indicating the presence of the nucleic acid construct in the expressed plasmid.

It should be noted that further modifications of the novel nucleic acid constructs were carried out during the preparation of the constructs in accordance with the procedures herein. It is apparent that the nucleic acid constructs have an efficient promoter to transcribe the polynucleotides or gene(s) in the relevant host cell. If the nucleic acid constructs were simply inserted into the plasmids employed herein, polynucleotide(s) would be transcribed by the plasmid Polymerase II (herein after Pol II) promoter. Since the Pol II promoter is next to the HindIII site and distal from the BamHI site, it is not known whether the nucleic acid sequences inserted into the BamHI site are transcribed from this promoter. In addition, transcription from the Pol II promoter in this instance would result in transcripts of uncertain size since there would not be termination sequences within the nucleic acid construct that would be recognized by the Pol II promoter. Also, promoters vary greatly in their promoter strength, and many promoters are regulated such that they are only "on" when induced by some stimulus.

The nucleic acid constructs of the present invention incorporate an RNA Polymerase III (herein after Pol III) promoter. The nucleic acid constructs incorporate a "box A" and a "box B" which comprise the Pol III promoter sequence. By constructing the nucleic acid constructs with an independent promoter, the genes can be transcribed independently of the plasmid promoter; therefore, the unregulated promoter should express constitutively in all animal cells or tissues. By using a Pol III promoter, the gene size is greatly reduced. This simplifies gene synthesis and allows the regulation of the amount of RNA produced simply by regulating the number of copies of the gene inserted into the vector. Further, Pol III promoters tend to be more or less universal in their expression and should function equally well in a wide range of host cell systems. Also, such promoters do not appear to have "enhancer" activity which are potentially carcinogenic.

The actual promoter sequence could have different embodiments, and is not limited herein by the previous description. For example, the promoter region including the upstream region, the transcription initiating region, "Box A" and "Box B" can be taken directly from any highly active, natural tRNA. A tRNA promoter sequence which has been shown to be particularly strong is the Glu tRNA gene, in mouse. The Glu tRNA gene has the advantage that it is straightforward to use as an active promoter and the short tRNA sequence which will be transcribed should not have any effect on the activity of the nucleic acid construct.

Another promoter sequence could involve upstream sequences from the promoter coming from a natural tRNA gene such as Glu tRNA, while transcriptional initiation sequences "Box A", Box B", and all intervening sequences could be supplied by the anti-sense RNA sequence itself with only relatively few base-pair substitutions. This has the advantage of economy and size which will facilitate synthesis and will allow maximum number of polynucleotides per vector. In addition, this promoter begins transcription precisely at the 5' end of the nucleic acid construct and ends transcription within several base pairs of the end of the nucleic acid construct sequence. This will be desirable where there is a need to minimize "extraneous" RNA sequences at the 5' and at the 3' ends of the resulting RNA molecule.

Such Pol III promoter constructs of the present invention should have a poly "T" site downstream from each Pol III promoter, i.e., which is the universal Pol III transcription termination signal. This site was included in the nucleic acid constructs to provide a transcription termination mechanism.

No molecular mechanism occurs with 100% efficiency. Furthermore, even those molecular mechanisms which normally have a very high efficiency can have poor efficiency under new circumstances. Therefore, optimal resistance will be achieved where more than one molecular mechanism is involved. Once a retrovirus has successfully inserted a single copy of its genome into a host's chromosome, there is no way to destroy it, except to destroy the cell. Therefore, it is especially desirable that the probability of this event can be reduced to an extremely low level. In certain alternative embodiments multiple polynucleotides were inserted into the same plasmid for transformation into a host cell system. The novel nucleic acid constructs were constructed with multiple Pol III promoters, e.g., "box A" and "box B", and polynucleotides inserted between the promoters.

Figure 15:
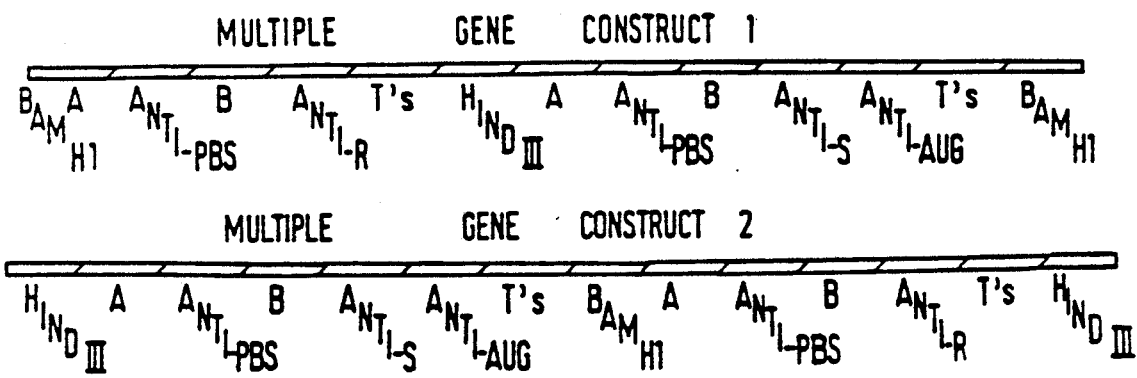
FIG. 15 is a schematic representation of Complex Gene Constructs 1 and 2 illustrating the Anti-sense polynucelotide structures of the present invention for insertion in either a BamHI or HindIII restriction site, respectively.

FIGS. 22-24 show the gene sequences of the polynucleotide/promoter combinations employed in the present invention using this multiple attack approach for the retroviruses HIV, HTLV-I, and FeLV, respectively. FIG. 15 illustrates the multiple nucleic acid constructs employed in the present invention utilizing the specific sequences shown in FIGS. 22-24, multiple promoters i.e., Box A and Box B, the pol III terminator sequence, and either a BamHI or HindIII end for insertion into the respective restriction site. The nucleic acid constructs have additional restriction endonuclease sites for insertion of further anti-sense producing gene fragments. Thus the nucleic acid constructs, when transcribed, will result in multiple short anti-sense fragments complementary to multiple essential hybridization sites within a retrovirus genome. This will affect the retrovirus at multiple hybridization sites which is believed to have a synergistic effect in inhibiting retroviral growth.

Figure 25:
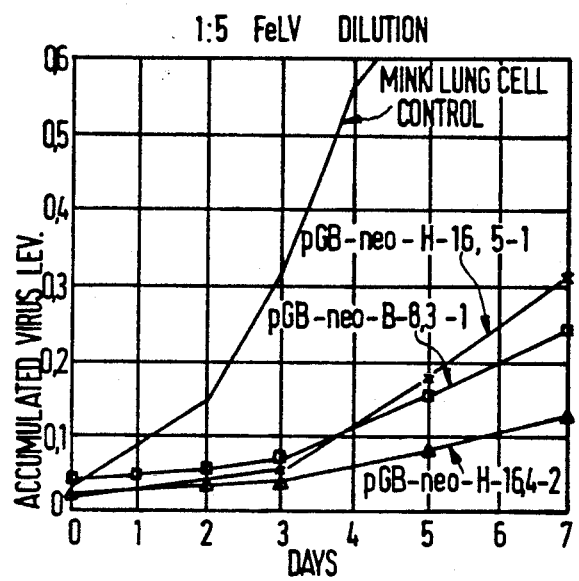
FIGS. 25 and 26 are a graph and corresponding chart illustrating Feline Leukemia ELISA results from data on the protective effects shown by cells containing the recombinant plasmids of the present invention following infection with Feline Leukemia virus at a 1:5 dilution.
Figure 26:
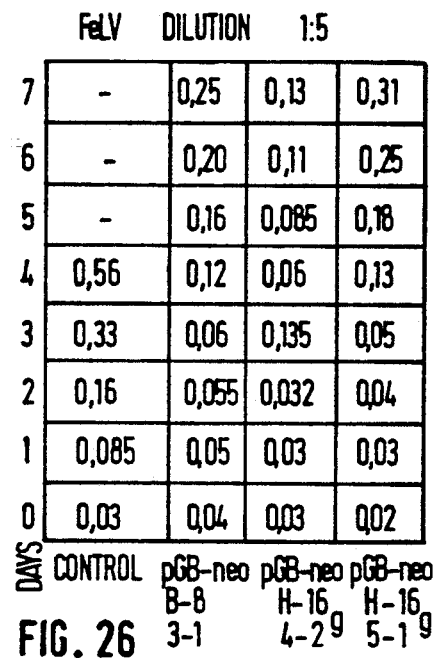

To illustrate the inhibition effect of the nucleic acid constructs in accordance with the present invention, transformed mink lung cells were challenged with Feline Leukemia Virus. The transformed cells were harvested under appropriate nutrient conditions. DME with 0.5 ug/ml of polybrine was mixed with the harvested cells to obtain the desired dilution of cells. The dilutions employed ranged from 1:5 to 1:50. The culture was incubated for 2 hours at 37° C. and the media was replaced with an amount of fresh media equivalent to the desired dilution. The FeLV was added at the appropriate dilution with polybrine and incubated overnight. The media was aspirated and the cells washed with 5 ml of fresh media. Then, 10 ml of DME only was added to each dish. The media was incubated with aliquots removed daily for testing the amount of virus present in the media. The ELISA test was used according to standard procedures in the art to test the amount of FeLV present in the media. Synbiotics Corp., *Feline Leukemia Virus Test Kit*, San Diego. A spectrophotometer reading was taken to quantify the results. The resulting data is summarized in FIGS. 25-32. The polynucleotide sequences used to illustrate the inhibition effects of the nucleic acid constructs include anti "R", anti "PBS", anti "AUG" and anti "S". Note, refer to FIGS. 16-19 for the construction of the Recombinant plasmids, wherein pGB-neo-H-16 was constructed according to FIG. 16, pGB-neo-H-17 was constructed according to FIG. 17; and pGB-neo-B-8 was constructed according to FIG. 19. The 1:5 dilution of FeLV in FIGS. 25 and 26 show that the mink lung cells, including the plasmid comprising the polynucleotide constructs, when challenged with the FeLV virus show an accumulation of virus ranging from 0.13 to 0.31 after seven days. This is significantly lower than the control of mink lung cells without the plasmid comprising the polynucleotide constructs showing an accumulated virus level of 0.56 after four days. These results show a significant decrease in accumulated FeLV virus levels when the mink lung cells are transformed with the nucleic acid constructs in accordance with the procedures and methods of the present invention. The tables, and graph label the cells pGB-neo-H-17, 5-1 (x); pGB-H-16, 4-2 (△) and pGB-neo-B-8, 3-1 (□). pGB-neo-H-17, 5-1 (x) contains sequences, than can be transcribed to RNA complementary to the "R", "PBS", "AUG" and "S" regions, as arranged in FIG. 15, construct 2, the actual nucleotide sequences as illustrated in FIG. 23. The plasmid designation as previously described indicates that these nucleic acid sequences were cloned into the Hind site of the vector. Plasmid #17 was selected to be used in transforming cells, and the resultant transformed cells 5-1 were chosen to be challenged with FeLV. pGB-neo-H-16, 4-2 ( ) contains sequences complementary to the "R", "PBS", "AUG", and "S" regions as arranged in FIG. 15, construct 2, the actual nucleotide sequences as illustrated in FIG. 23. The plasmid designation indicates that these nucleic acid sequences were cloned into the Hind site of the vector. Plasmid #16 was selected to be used in transforming cells, and the resultant transformed cells, 4-2, were chosen to be challenged with FeLV. pGB-neo-B-8, 3-1 (□) contains sequences, that can be transcribed to RNA complementary to this "R", "PBS", "AUG", and "S" regions, as arranged in FIG. 15, construct 1, and actual nucleotide sequences as illustrated in FIG. 23. Plasmid designation indicates that these nucleic acid sequences were cloned into the Bam site of the vector, plasmid #8 was selected to be used in transforming cells, and the resultant transformed cells, 3-1, were chosen to be challenged with FeLV.

Figure 27:
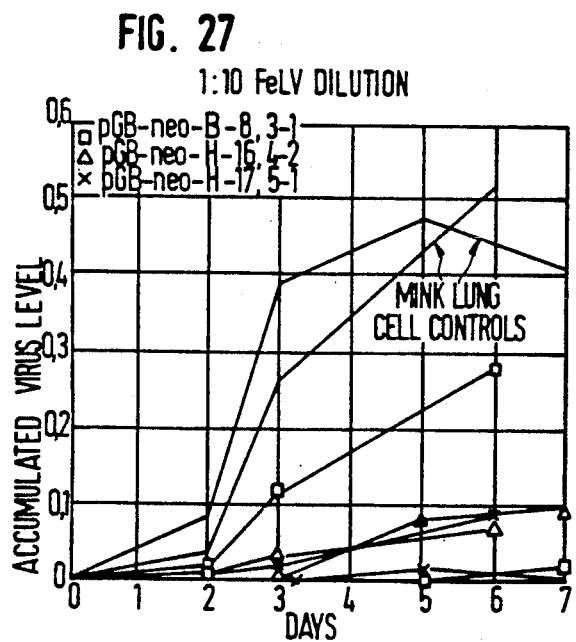
FIGS. 27 and 28 are a graph and corresponding chart illustrating Feline Leukemia ELISA results from data on the protective effects shown by cells containing the recombinant plasmids of the present invention following infection with Feline Leukemia virus at a 1:10 dilution.
Figure 28:
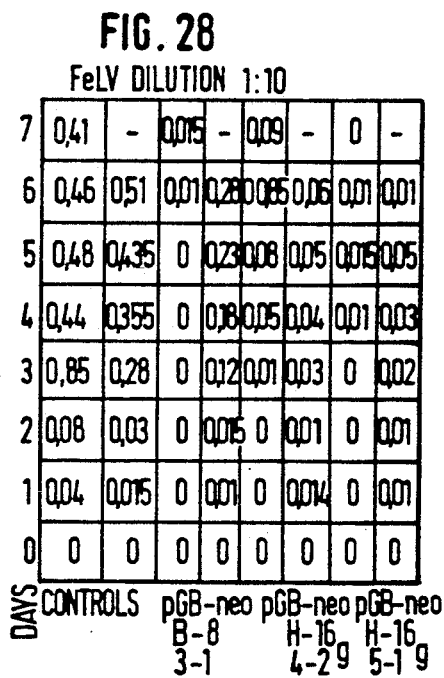

The 1:10 dilution of FeLV in FIGS. 27 and 28 show that the mink lung cells, including the plasmid comprising the polynucleotide constructs, when challenged with the FeLV virus show an accumulation of virus ranging from 0.01 to 0.28 after six days. This is significantly lower then the control of mink lung cells without the plasmid comprising the polynucleotide constructs showing an accumulated virus level of 0.46 to 0.51 after six days. These results show a significant decrease in accumulated FeLV virus levels when the mink lung cells are transformed with the nucleic acid constructs in accordance with the procedures and methods of the present invention.

Figure 29:
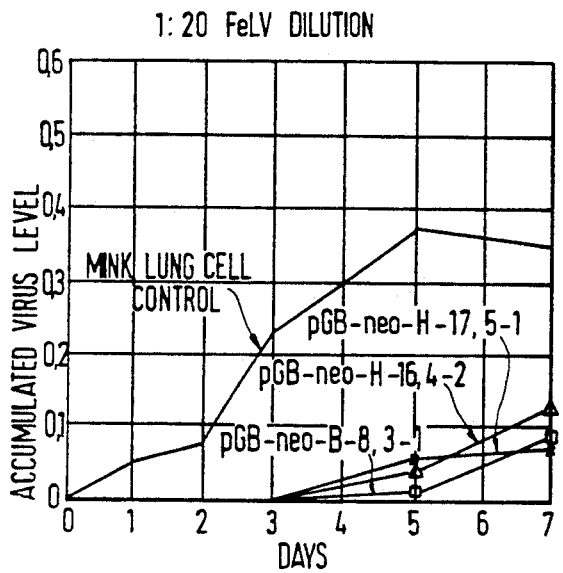
FIGS. 29 and 30 are a graph and corresponding chart illustrating Feline Leukemia ELISA results from data on the protective effects shown by cells containing the recombinant plasmids of the present invention following infection with Feline Leukemia virus at a 1:20 dilution.
Figure 30:
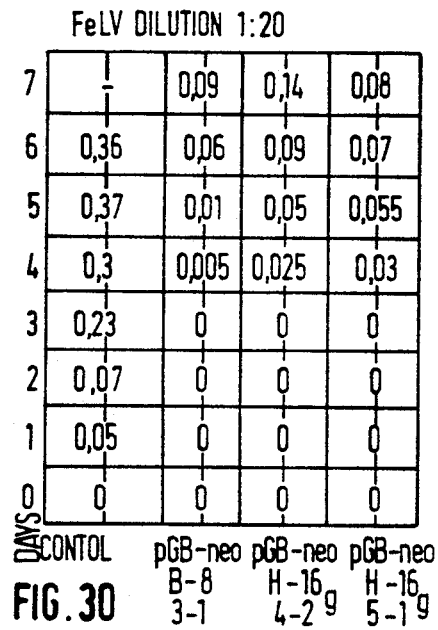

The 1:20 dilution of FeLV in FIGS. 29 and 30 show that the mink lung cells, including the plasmid comprising polynucleotide constructs, when challenged with the FeLV virus show an accumulation of virus ranging from 0.08 to 0.14 after seven days. This is significantly lower then the control of mink lung cells without the plasmid comprising the polynucleotide constructs showing an accumulated virus level of 0.36 after six days. These results show a significant decrease in accumulated FeLV virus levels when the mink lung cells are transformed with the nucleic acid constructs in accordance with the procedures and methods of the present invention.

Figure 31:
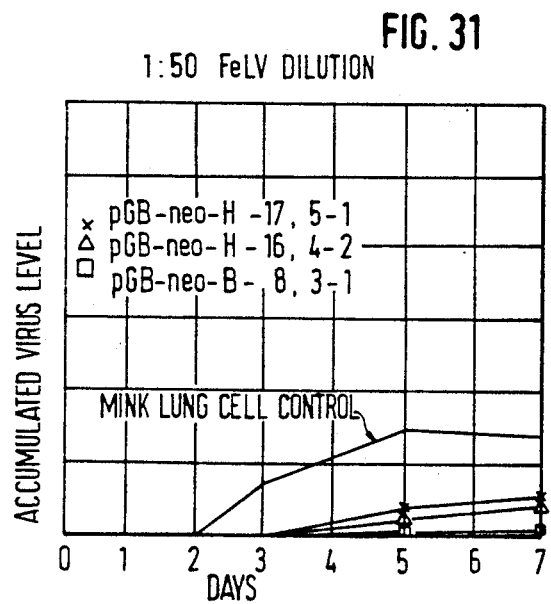
FIGS. 31 and 32 are a graph and corresponding chart illustrating Feline Leukemia ELISA results from data on the protective effects shown by cells containing the recombinant plasmids of the present invention following infection with Feline Leukemia virus at a 1:50 dilution.
Figure 32:
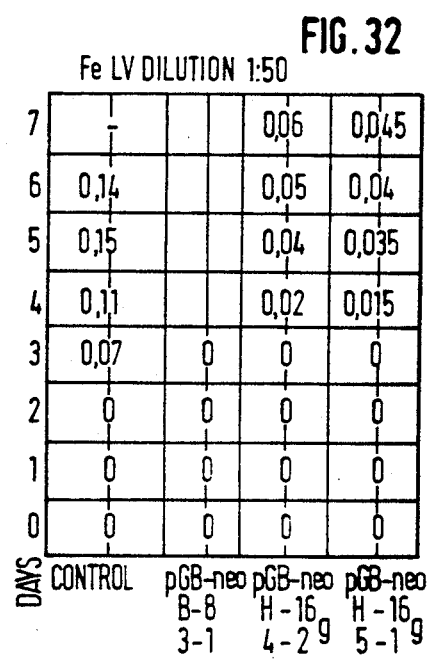

The 1:50 dilution of FeLV in FIGS. 31 and 32 show that the mink lung cells, including the plasmid comprising the polynucleotide constructs when challenged with the FeLV virus show an accumulation of virus ranging from 0.045 to 0.06 after seven days. This is significantly lower then the control of mink lung cells without the plasmid comprising the polynucleotide constructs showing an accumulated virus level of 0.14 after six days. These results show a significant decrease in accumulated FeLV virus levels when the mink lung cells are transformed with the nucleic acid constructs in accordance with the procedures and methods of the present invention.

EXAMPLE 2

Another preferred novel nucleic acid construct in accordance with the present invention is a synthesized double-stranded DNA sequence operatively linked to the SV40 early promoter sequence contained within a retroviral vector. The nucleic acid construct (Anti-PBS Gene Construct, as shown in FIG. 9) is transcribed into an anti-sense RNA molecule which is complementary to the LTR-primer binding site within the retroviral genome.

Copies of the nucleic acid construct were synthesized by amplification using the polymerase chain reaction. The nucleic acid constructs were cut to blunt ends using Nae I and Sma I. The nucleic acid constructs were then cloned into the retroviral vector LNSX (a gift of Dr. D. Miller, Seattle) which had been previously cut with Stu I. The inserts have been cloned in both the normal and reverse transcriptional orientation, as determined by dideoxy sequence analysis, downstream of the SV40 early promoter sequence in LNSX. Stably transfected mink lung cell lines were prepared by the introduction of the LNSX-nucleic acid constructs, containing the insert in the reverse transcriptional orientation, using the calcium phosphate method of transfection as described in Example 1. Transfectants were selected for by neomycin resistance with the presence of G418 in the tissue culture medium, since the retroviral vector contains the neo gene.

Figure 35:
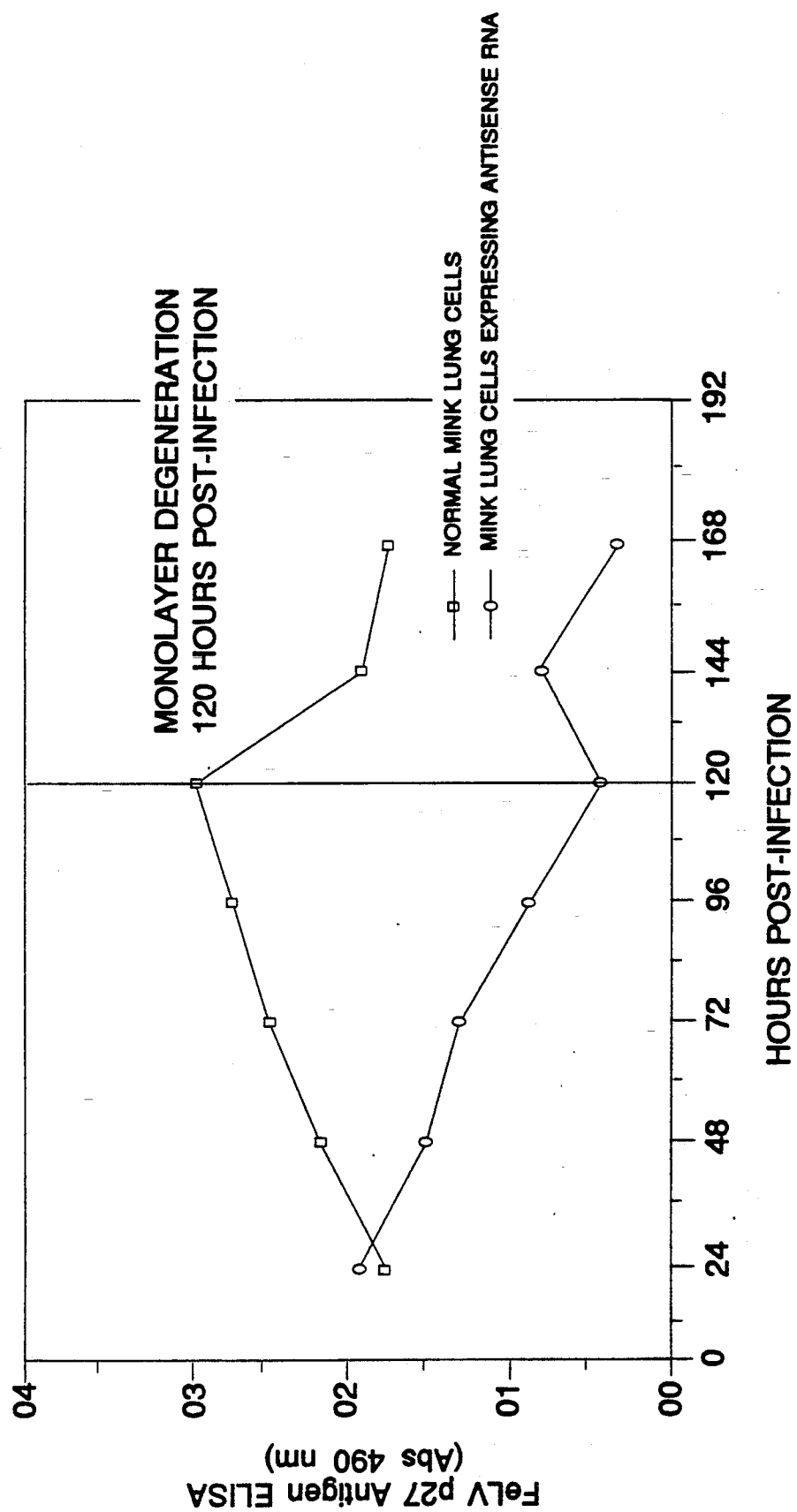
FIG. 35 is a graph showing the results of a FeLV p27 antigen ELISA following a FeLV challenge to normal mink lung cells, and cells expressing anti-sense RNA of the present invention.

To evaluate the resistance to FeLV of a cell line containing the nucleic acid construct in a retroviral vector, confluent monolayers of normal and transfected mink cells were challenged with the EECC strain of FeLV. Inhibition of FeLV replication was measured for 168 hours post-infection by monitoring p27 core antigen levels in ELISA (abs 490 nm). FIG. 35 shows the p27 antigen levels of normal mink lung cells ( -- ) and of mink lung cells stably transfected with the LNSX-nucleic acid constructs expressing antisense sequence to the LTR-primer binding site (---). At 120 hours post-infection, a significant inhibition of FeLV replication was observed in the transfected cells compared to normal mink lung cells. The inhibition was reflected by a 84% reduction in FeLV p27 core antigen production. Since after 120 hours post-infection the normal cells were killed by FeLV, meaningful comparisons of virus production could not be made after this time.

Although this embodiment describes transfection of the mink lung cells with the retroviral vector, feline cat embryo cells (NCE) have been successfully infected with retroviral vector which had been generated from a commercially available packaging cell line. Since NCE cells containing the retroviral vector with insert are selected for in the presence of G418 in the culture media, these cells could be used as an alternative to mink lung cells for antisense RNA inhibition studies.

EXAMPLE 3

Yet another preferred embodiment of the invention, comprises the inhibition of viral replication using novel nucleic acid constructs in cells which were subsequently challenged with HIV. The novel nucleic acid construct can be transcribed into a RNA molecule complementary (anti-sense) or corresponding to nucleic acid segments within the retroviral genome essential to retroviral replication including the LTR, the AUG start codon regions, RNA splice sites, the U5 region, the U3 region, the PBS region, the cap site, the TAT splice site, the ART splice site, the leader region, and the polyP region. The polynucleotides comprising the nucleic acid construct are depicted in FIG. 22.

The polynucleotides were synthesized according to the procedures described in Example 1. The nucleic acid construct, containing the polyncleotides, was cloned into either the BamHI or HindIII site of pRSVneo. The plasmid preparations tested also included pRSVneo by itself as a control. Aliqouts of HUT 78 cells, containing approximately $1.2 \times 10^8$ cells, were electroporated with 40 ug/ml of the respective plasmid preparation. The electroporation parameters included a 0.5 ml volume, a time constant of 1.25 usec, a voltage of 5.0 kV/cm, and a capacitance of 10 ufd. An additional control included HUT 78 cells which did not contain any plasmid, i.e. were not electroporated with pRSVneo. $1 \times 10^6$ electroporated (greater than 72 hours post-electroporation) HUT 78 cells or control cells in one milliliter of growth medium was mixed with a one ml suspension of HIV containing $10^2$ TCID$_{50}$ dose infectious virus in the presence of 2 ug/ml polybrine. After one hour of incubation at 37° C., the cells were washed and placed in culture in 10 ml complete growth medium containing RPMI 1640 supplemented with 10% fetal bovine serum and antibiotics. Virus replication was monitored by reverse transcriptase activity, HIV-1 p24 antigen capture assay, and an immunofluorescence assay.

The reverse transcriptase activity assay was performed by centrifuging the cell cultures to pellet the cells. Virus pellets were prepared from the supernatants by centrifuging the supernatants at 40,000 rpm for 30 minutes. Virus was disrupted to release the reverse transcriptase from its core by incubation in virus solubilization buffer containing 0.05% Triton X-100 in TNE buffer. Solubilized virus was combined in a mixture containing magnesium ion, template primer [poly(ra) p(dt)], tritium labeled thymidine 5'-trriphosphate disodium (dATP), and dithiothreitol (DTT) in Tris buffer, pH7.8. The mixture was incubated at 37° C. for 2 hours, after which tRNA and trichloroacetic acid were added to clump the DNA and precipitate the reaction products. This solution was filtered through glass filter circles, and the filters were then washed with trichloroacetic acid. The DNA was trapped on the filter, whereas the unincorporated label was washed through the filter. The filters were dried and placed in scintillation fluid.

The amount of radioactivity in the DNA was determined by using a beta scintillation counter.

HIV-1 p24 antigen produced in the tissue culture fluid was measured by the Retro-Tek HIV p24 antigen ELIISA (Cellular Products) according to the manufacturer's directions. Briefly, the wells of a microtiter plate were coated with antibody fractions obtained from human sera which exhibited high titers of anti-HIV antibody. These antibodies were polyvalent and predominantly reacted with the major gag gene products of HIV as determined by Western blot immunoassays. Viral antigen was specifically captured on to the immobilized antibody after a simple incubation step. Captured antigen was then allowed to react with a mixture of p24-specific monoclonal antibodies previously conjugated to biotin. Following a subsequent incubation with streptavidin- peroxidase reagent, color development of the bound enzyme was observed using the appropriate substrate. Resultant optical densities are proportional to the relative amount of viral p24 antigen contained within the test samples.

To prepare slides for immunofluorescence assay, approximately $1 \times 10^6$ cells were pelleted, washed three times with PBS, and fixed in 2% paraformaldehyde (in PBS) at room temperature for 30 minutes. After the fixation, cells were washed again and resuspended in PBS. Resuspended cells were dotted on the slide, air-dried, and fixed with cold acetone for 10 minutes. Slides were then washed in PBS and air-dried. To the fixed cells of each slide was applied 30 ul of human HIV-1 positive serum which had been diluted to an appropriate dilution in 20% normal goat serum in PBS. The slides were then incubated at 37° C. for 90 minutes in a moist chamber after which the slides were washed three times in PBS and air-dried. Biotinylated F(ab')$_2$ of goat anti-human IgG and IgM (heavy and light chains) was applied to each dot and incubated for 60 minutes at 37° C. Following this incubation, the cells were washed with PBS, air-dried, and then reacted with 30ul of streptavidin-FITC (fluoroscein isothiocyanate) conjugate at 37° C. for 15 minutes. Smears were washed with PBS and observed with a fluorescence microscope.

Inhibition of viral replication using the nucleic acid construct of this embodiment of the present invention is represented in Table II.

TABLE II

| Cell Line | 12 days post-challenge | | | 20 days post-challenge | | |
|---|---|---|---|---|---|---|
| | IFA | RT | p24 | IFA | RT | p24 |
| HUT 78 - no plasmid | | | | | | |
| 1 | − | − | − | − | − | − |
| 2 | − | − | − | − | − | − |
| HUT 78 - pRSVneo with no insert | | | | | | |
| 1 | +/− | + | +/− | − | − | − |
| 2 | + | + | + | − | − | − |
| 1 | − | − | − | − | − | − |
| 2 | − | − | − | − | − | − |
| 1 | +/− | + | + | +/− | + | +/− |
| 2 | + | + | + | + | + | + |
| 1 | +/− | +/− | +/− | − | − | − |
| 2 | + | + | + | − | − | − |
| HUT 78 with: | | | | | | |
| pRSVneoBam | − | − | − | − | − | − |
| | − | − | − | +/− | − | − |
| pRSVneoHind | + | +/− | + | + | + | + |
| | + | + | + | + | + | + |
| pRSVneoBam | − | − | − | − | − | − |
| | − | − | − | − | − | − |
| pRSVneoHind | + | + | + | − | − | − |
| pRSVneoBam | + | + | + | +/− | + | +/− |
| | − | − | − | − | − | − |
| pRSVneoHind | − | − | − | − | − | − |
| pRSVneBam | − | − | − | − | − | − |
| | + | +/− | +/− | − | − | − |

+: resistant to HIV-1 challenge
+/−: partially resistant
−: not resistant

These results are encouraging in that in some cases, the nucleic acid construct, which can encode potential anti-sense RNA for interference hybridization, showed significant anti-viral protection. However, one third of the constructs tested show little or no protection. Further studies are needed to determine if the lack of protection is due to the orientation of the polynucleotides in relation to the plasmid promoter or some other as yet to be determined factor. In addition, sometimes the controls containing the plasmid with no insert seemed to show some inhibition. Further analysis is required to determine if this observation is an artifact or some non-specific effect due to the plasmid itself.

EXAMPLE 4

Human Bone Marrow Auto-Transplant

This embodiment is in accordance with the procedures and methods described in Example 1 or 2. Auto-transplant of bone marrow (i.e., re-introducing a patient's own bone marrow cells) is now a relatively minor and routine procedure. Bone marrow cells are extracted by syringe, and in the present case, transformed and cultured. The patient is then irradiated, or otherwise treated, to destroy existing bone marrow cells remaining in the patient. Then the transformed cultured bone marrow cells are injected back into the patient's circulatory system. Such cells eventually migrate back into the bone marrow, re-establishing that tissue.

In order to make all of the lymphocytes of a patient immune to the AIDS related virus, bone marrow cells would be transformed with the nucleic acid constructs of the present invention by any of the methods already discussed, and transformed cells would be selected for. Multiple nucleic acid constructs can be employed. Preferably, the polynucelotide sequence(s) employed in the constructs will direct transcription of RNA complementary or corresponding to the R region, the primer binding site (PBS) with a false leader and a false primer coding sequence, the first splice region and/or the AUG site. Non-transformed bone marrow within the patient would be destroyed and the transformed bone marrow cells would be used to re-establish the bone marrow tissue. As a result, all lymphocytes, including T4 cells, deriving from the transformed bone marrow would be immune to the virus. Consequently, the virus would be eradicated from the patient's system. It should be noted that irradiation of the patient may not be necessary since the AIDS pathology results in killing of infected cells by the HIV virus itself thus reducing the infected T4 cell population.

Auto-transplant can be performed in both human and other mammalian, e.g., feline systems. In cats, the germ-line of the animal might be transformed to produce virus resistant strains (breeds) of cats.

EXAMPLE 5

Injection of Transformed Liposomes

Alternatively, transformation can be accomplished in situ by encapsulating constructs of the present invention into liposomes using established methods, binding commercially available antibodies to the surface of the liposomes which specifically bind to T4 cells, and injecting these liposomes into the blood stream of the patient. The antibody-targeted liposomes will bind to T4 cells, and will continually be absorbed by the cell, leading to transformation. Subsequently, transformed T4 cells will have a selective advantage over non-transformed cells, due to their immunity to virus. Such resistant cells will multiply as susceptible cells are killed off by the virus. This selection process can be enhanced by use of selective agents (i.e., antibiotics) favoring the transformed cells. This method would be especially appropriate for AIDS patients who could not tolerate a bone marrow transplant (see above).

This embodiment is in accordance with the procedures and methods described in Example 1, and can utilize multiple genes in multiple copies, with Pol III promoters. Preferably, the polynucleotide sequence(s) employed in the constructs will direct transcription of RNA complementary or corresponding to the R region, the primer binding site, the first splice site region and/or AUG start codon region.

EXAMPLE 6

Blocking of Reverse Transcription Using an Anti-sense RNA Molecule Complementary to the "R" Region.

This embodiment is in accordance with the procedures and methods described in Example 1. As already described, the R region, found at both ends of the retroviral RNA genome, plays a crucial role in the "first jump" of reverse translation. Reverse transcription becomes stalled at the 5' end of the virus and must be carried to a new template at the 3' end of the virus. This is possible because the enzyme is attached to the cDNA strand which has been transcribed from the 5' R region. This cDNA is naturally complementary to R and can hybridize to the 3' R region. This results in a bridge which circularizes the virus and allows reverse transcription to continue.

This "first jump" can be blocked by an independent RNA molecule which is complementary to the R region. This molecule transcribed from nucleic acid construct, is referred to as "Anti-R". This molecule can hybridize to the 3' R region and will block the 5'-3' bridge from forming between the two ends of the virus. Such hybridization tends to be stable, such that competition for the R hybridization site is on a first-come basis. Since reverse transcription is a particularly slow process, the cDNA molecule transcribed from the 5' end of the virus will not be available until some time after initial cell infection. Therefore, if abundant independent RNA molecules are already present in the cell, and are complementary to R, there will be a very high probability that the R site will be blocked (bound) by them, before the "first jump" is even possible. Consequently, this will preclude successful infection of the cell by that viral strand. Refer to FIGS. 6–8 for the sequence of the Anti-R nucleic acid constructs of the HTLV-1, FeLV, and HIV viruses respectively.

The R region of retroviruses is the most highly conservative (unchanging) region. However, point mutations do occur in this region. Different R region sequences of different HIV strains show several minor nucleotide differences in this region. Newly arising mutant strains will also have small differences in this region. This is not an important consideration, since nucleic acid hybridization does not require perfect base-pairing. Likewise, the interfering molecule may have additional sequences 5' and 3', or may be less than length at the R region. The relevant point is that any such novel nucleic acid constructs, as herein described, can direct transcription of complementary RNA which can stably hybridize to the R region of the virus, even though base pairing is less than 100%. not complete.

EXAMPLE 7

Blocking the Primer Binding Site (PBS) and Adjacent Sequences Using Anti-Sense RNA This embodiment is in accordance with the procedures and methods described in Example 1. This novel nucleic acid construct, when transcribed, produces complementary RNA that can bind to the primer binding site region (herein after "Anti-PBS"). As a result, the complementary RNA will compete with the tRNA(Lys)/reverse transcriptase samples for this site, thereby blocking initiation of reverse transcription. In addition, it will bind to the double-strand DNA which is involved in the "second jump" of reverse translation. This will block completion of reverse translation in a similar way as the first two anti-viral molecules. Because of complementation to the 3' end of the U5 region, RNA from this construct may also affect circularization and insertion into the chromosome of the double-stranded viral DNA. Refer to FIGS. 9–11 for the sequences of the Anti-PBS gene constructs of the FeLV, HTLV-1 and HIV viruses respectively.

EXAMPLE 8

Anti-Sense RNA Complement to the Poly-Purine Sequence and Adjacent Sequences.

This embodiment is in accordance with the procedures and methods described in Example 1. This novel nucleic acid construct includes the 5' end of the U3 region. The construct, when transcribed, produces RNA complementary to the single-strand DNA, in the region where second strand DNA synthesis begins. If in a RNA form, and if associated with improper flanking sequences, this molecule will bind in the initiation region of second strand DNA synthesis and will block proper synthesis of the double-strand DNA.

EXAMPLE 9

Blocking of the First RNA Splice Site and the First AUG Start Codon Site

This embodiment is in accordance with the procedures and methods described in Example 1. Many RNA molecules must have intervening sequences removed or "spliced out" before they can be properly translated into protein. The HIV virus has at least four "splice" sites. Splicing at such sites is required for translation of several proteins downstream of GAG. Such splicing involves precise recognition of RNA single-stranded sequences by proper enzymes. Nucleic acid constructs producing complementary RNA capable of hybridizing in such regions will prevent proper splicing and thereby prevent proper protein translation (herein after "Anti-SD). Near the same region is the first AUG site, where translation of GAG protein begins. This site is also subject to hybridization interference, since protein translation can not be initiated in a region of double-stranded RNA (herein after "Anti-AUG"). Therefore, complementary RNA molecules spanning these two regions will block translation of GAG protein as well as the other proteins further downstream. Refer to FIGS. 12-14 for the Anti-AUG and Anti-S sequences of FeLV, HTLV-1, and HIV viruses.

As will be seen the RNA molecules already described can be predicted to have additional anti-HIV activity by interfering with additional viral mechanisms. The multi-functional nature of these molecules is important in establishing multiple lines of defense. These are described below:

EXAMPLE 10

Blocking Circulation and Chromosomal Insertion

This embodiment is in accordance with the procedures and methods described in Example 1. The precise mechanisms involved in circularization and chromosomal insertion are unknown, although the 5' and the 3' ends of the virus are obviously involved. The short inverted repeats at these ends presumably allow end-to-end hybridization. It is noteworthy that certain complementary nucleic acid constructs described herein include the inverted repeat at the 5' end of the DNA virus, and the inverted repeat at the 3' end of the DNA virus. Therefore, nucleic acid constructs already described provide potential interfering mechanisms for the viral insertion processes.

EXAMPLE 11

Blocking DNA Transcription/Transation

This embodiment is in accordance with the procedures and methods described in Example 1. Some retroviruses, like HIV, have a specific open reading frame which codes for a transcriptional activator TAT protein. In the absence of this protein, the pro-virus is not transcribed and/or translated (has been controversial), and all viral activities cease. Translation of this protein will be blocked by previously described nucleic acid constructs. Specifically, the Anti-SD and the Anti-AUG nucleic acid constructs can be targeted to block synthesis. Consequently nucleic acid constructs already described can be used to block transcription and/or translation by blocking synthesis of the transcriptional activator protein.

EXAMPLE 12

Blocking of the RNA Packaging Site

This embodiment is in accordance with the procedures and methods described in Example 1. A region of the viral RNA that is essential for packaging of the RNA into infectious particles has been shown in other retroviruses to be between the first splice site and the GAG coding region. It appears that this region binds to one of the GAG proteins. This region is included in the region complemented by the Anti-SD and the Anti-AUG nucleic acid constructs. Therefore, the previously described constructs may be used to block RNA packaging, as well as blocking RNA splicing and translation.

EXAMPLE 13

Blocking the Poly-A Attachment Site

This embodiment is in accordance with the procedures and methods described in Example 1. Retroviral RNA is normally processed, like other mRNA's, by enzymatic splicing of a poly-A tail on the 3' end of the molecule. This is considered important for transport of the RNA out of the nucleus, and for stability in the cytoplasm. The previously described "anti-R" nucleic acid construct can produce complementary RNA capable of binding to the poly-A attachment site and interfere with such RNA processing in this region.

EXAMPLE 14

Blocking of Dimer Formation and Genomic Folding

This embodiment is in accordance with the procedures and methods described in Example 1. Infectious retroviral particles contain two identical RNA genomic molecules which have regions of mutual hybridization i.e., dimer formation. They have as well, regions of internal hybridization and folding within each molecule. The exact role of these 3-dimensional configurations is unclear, but they appear to be universal and therefore important. The area of dimerization between the two molecules is in the U5, primer binding site, and leader regions. Therefore the previously described nucleic acid constructs should block dimer formation and should interfere with internal hybridization and folding, within the individual molecules.

While the above-mentioned anti-viral molecules are simple complements of different regions of the retroviruses, more complex nucleic acid constructs can be employed to enhance anti-viral activity. These are described below:

EXAMPLE 15

Compound Genes

This embodiment is in accordance with the procedures and methods described in Example 1. Compound nucleic acid constructs can be synthesized which will code for mRNA consistinq of tandem repeats of the same anti-viral sequence, or chimeric mRNA's containing more than one anti-viral sequence. By this method, the same promoter can transcribe proportionately more anti-viral material. Chimeric mRNA may have the added anti-viral trait of cross-linking different parts of the virus, disrupting genomic structure and function.

EXAMPLE 16

False Templates

This embodiment is in accordance with the procedures and methods described in Example 1. The reverse transcriptase enzyme of the virus can be used against itself, through the use of false templates. As already mentioned, certain RNA sequences serve as initiation sites for reverse transcription (i.e., the primer binding site, herein after PBS), or serve as re-initiation sites for reverse transcription (i.e., the R region, and the PBS region, at the first and second jump events, respectively). Reverse transcription normally begins from these sequences, and any sequence 5' from these sequences will be automatically reverse transcribed. By adding inappropriate sequences 5' to the R and PBS sites as previously described, false templates are created. These false templates have the original anti-viral activities of the R and PBS molecules. In addition, they have several new properties: a) In the case of initiating reverse transcription, the PBS false template will bind and "disarm" reverse transcriptase complexes; b) In terms of re-initiating reverse transcription after the first and second jumps, false templates will lead the reverse transcription process down a "false path", leaving the original template destroyed, and the new cDNA abortive; c) Because the false templates will be reverse-transcribed, cDNA complementary to the 5' end of the molecule will be created by the reverse transcriptase enzyme. The resulting DNA sequence may have still further anti-viral activity. For example, if the 5' RNA sequence employed in the false template was a complement of the poly-purine tract, the resulting cDNA would be the DNA equivalent of the poly-purine tract, which would stably bind to the initiation site for second strand DNA synthesis, blocking correct initiation of DNA synthesis from this point.

EXAMPLE 17

False Primers

This embodiment is in accordance with the procedures and methods described in Example 1. False primers can be created by placing a lysine tRNA sequence at the 5' end of any of several of the types of nucleic acid constructs already discussed. The result will be a modified lysine tRNA, which will have lost its original site for binding to the PBS. Instead, the modified lysine tRNA will bind at a different part of the viral genome, as dictated by the specific complementary "tail" selected. Consequently, the resulting false primer will complex with reverse transcriptase enzyme, and will initiate reverse transcription at an improper site. This will cause the viral template to be progressively degraded from that point, and will result in abortive and non-infectious cDNA with improper "ends" required for circularization and insertion.

While most anti-sense nucleic acid constructs involve Hybridization Interference between nucleic acids, there are a few resistance mechanisms involving protein gene products. These are described below for HIV:

EXAMPLE 18

Creation of a Transcriptional or Translational Repressor Protein Specific for the HIV R Region This embodiment is in accordance with the procedures and methods described in Example 1. The TAT protein has been shown to be essential to HIV translation and replication, by binding to the R region. The TAT protein, if modified, could be changed into a repressor protein, which would bind the same site, but would block translation rather than induce it. This would be done by sub-dividing the protein into its functional domains, and deleting the activator domain or mutating it, or by sub-cloning the domain responsible for recognizing and binding to the viral R region. For example, the arginine-rich region in the second half of the activator protein sequence is a likely region, important in the RNA binding process. The second half of this protein sub-domain might adequately compete with the fully functional protein for the binding site, thereby acting as a repressor. In addition, bulky DNA interactive amino acid chains might be added to the DNA-binding sub-domain, to further interfere with initiation of translation or transcription in this region of RNA or DNA.

EXAMPLE 19

Creation of a Self-destruct Gene

This embodiment is in accordance with the procedures and methods described in Example 1. The fact that the HIV is self-activating provides an excellent opportunity to engineer a "hyper-sensitive" form of resistance. By combining the natural HIV promoter and "R" Sequence with a sequence coding for any type of lysis protein (which would come from a number of sources), a "self-destruct" mechanism is created for the cell. Upon initial infection of the cell, the viral activator protein is produced, which will activate the HIV virus promoter, leading to production of the lysis protein and destruction of the cell before the virus has an opportunity to reproduce. This mechanism might be suitable for use very early in infection, or after bone marrow substitution, or as a backup mechanism in conjunction with genes blocking the initial infection process.

EXAMPLE 20

The ENV Protein

This embodiment is in accordance with the procedures and methods described in Example 1. There is evidence that the gene of the ENV protein of retroviruses can condition resistance, if expressed constitutively in the cell. In this case, a host cell is transformed with a ENV gene construct. The resulting RNA is translated into ENV protein, which binds to, and saturates, the cell surface antigens of the cell. Because the binding sites are already saturated, viral particles can not bind to and infect the cell.

From the foregoing, it will be obvious to those skilled in the art that various modifications in the above-described methods, constructs and cells can be made without departing from the spirit and scope of the invention. Accordingly, the invention may be embodied in other specific forms without departing from the spirit or essential characteristics thereof. Present embodiments and examples, therefore, are to be considered in all respects as illustrative and not restrictive, the scope of the invention beinq indicated by the appended claims rather than by the foregoing, and all changes which come within the meaning and range of equivalency of the claims are therefore intended to be embraced therein.

We claim:

1. A method of conferring resistance to retroviral infection upon a host cell by inhibiting in the infection process at least one step of the process selected from the group consisting of retroviral replication, reverse transcription, and translation, said method comprising:

Introduction into said host cell in vitro of a vector comprising a polynucleotide which is transcribed to RNA, within said host cell, said RNA is complementary to a nucleic acid sequence within at least one region within the genome of said retrovirus, wherein said region is an essential hybridization site within the retroviral genome selected from the group consisting of the 3′R-region, the primer binding (PBS) region, the AUG start codon region, and RNA splice sites; and wherein said retrovirus is feline leukemia virus (FeLV).

2. The method of claim 1, wherein said polynucleotide is a synthetic polynucleotide.

3. The method of claim 1, wherein said polynucleotide is DNA.

4. The method of claim 1, wherein said vector is selected from the group consisting of a viral vector, a retroviral vector and a plasmid.

5. The method of claim 4, wherein said vector is a plasmid.

6. The method of claim 1, wherein said polynucleotide directs transcription of a single RNA which is complementary to the multiple hybridization sites within the retrovirus genome.

7. The method of claim 4, wherein said vector further comprises a first promoter which controls transcription of said RNA within said host cell.

8. The method of claim 4, wherein said vector further comprises a first terminator which controls termination of transcription of said RNA within said host cell.

9. The method of claim 4, wherein said vector further comprises a marker for selection of transformed cells.

10. The method of claim 7, wherein said polynucleotide further comprises a second promoter which controls transcription of said RNA within said host cell.

11. The method of claim 10, wherein said promoter is RNA Polymerase III promoter.

12. The method of claim 8, wherein said polynucleotide further comprises a second terminator which controls termination of transcription of said RNA within said host cell.

13. The method of claim 12, wherein said terminator is a RNA Polymerase III terminator sequence.

14. A nucleic acid construct conferring resistance to retroviral infection upon a host cell by inhibiting in the infection process at least one step of the process selected from the group consisting of retroviral replication, reverse transcription, and translation, said construct comprising a polynucleotide which when introduced by a vector into the host cell in vitro results in transcription of the polynucleotide into RNA complementary to the nucleic acid sequences within multiple regions within the genome of said retrovirus, wherein said regions are essential hybridization sites within the retroviral genome consisting of the 3'R-region, the primer binding (PBS) region, the AUG start codon region, and RNA splice sties of said retrovirus; and wherein said retrovirus is FeLV.

15. The nucleic acid construct of claim 14, wherein said polynucleotide is a synthetic polynucleotide.

16. The nucleic acid construct of claim 14, wherein said polynucleotide is DNA.

17. The nucleic acid construct of claim 14, wherein said vector is selected from the group consisting of a viral vector, a retroviral vector and a plasmid.

18. The nucleic acid construct of claim 17, wherein said vector is a plasmid.

19. The nucleic acid construct of claim 17, wherein said vector further comprises a first promoter which controls transcription of said RNA within said host cell, and a first terminator which controls termination of said transcription.

20. The nucleic acid construct of claim 17, wherein said vector further comprises a marker for selection of transformed cells.

21. The nucleic acid construct of claim 19, wherein said polynucleotide comprises a second promoter which controls transcription of said RNA within said host cell.

22. The nucleic acid construct of claim 21, wherein said promoter is RNA Polymerase III promoter.

23. The nucleic acid construct of claim 19, wherein said polynucleotide comprises a second terminator which controls termination of transcription of said RNA within said host cell.

24. The nucleic acid construct of claim 23, wherein said terminator is a RNA Polymerase III terminator sequence.

25. An RNA molecule, produced from the transcription of a polynucleotide of a vector which has been introduced into a host cell in vitro, said RNA molecule (a) confers resistance to retroviral infection upon a host cell by inhibiting in the infection process at least one step of the process selected from the group consisting of retroviral replication, reverse transcription, and translation; and (b) is complementary to the nucleic acid sequences within multiple regions within the genome of said retrovirus, wherein said regions are essential hybridization sties within the retroviral genome consisting of the 3'R-region, the primer binding (PBS) region, the AUG start codon region, and RNA splice sites of said retrovirus, and wherein said retrovirus is FeLV.

26. The RNA molecule of claim 25, wherein said vector further comprises a first promoter which controls transcription of said RNA within said host cell.

27. The RNA molecule of claim 25, wherein said vector further comprises a first terminator which controls termination of transcription of said RNA within said host cell.

28. The RNA molecule of claim 25, wherein said vector further comprises a marker for selection of transformed cells.

29. The RNA molecule of claim 26, wherein said polynucleotide comprises a second promoter which controls transcription of said RNA within said host cell.

30. The RNA molecule of claim 27, wherein said promoter is RNA Polymerase III promoter.

31. The RNA molecule of claim 27, wherein said polynucleotide comprises a second terminator which controls termination of transcription of said RNA within said host cell.

32. The RNA molecule of claim 31, wherein said terminator is a RNA Polymerase III terminator sequence.

33. A cell modified by the method of claim 1.

34. Progeny of the cell of claim 33.

* * * * *